United States Patent
Yu et al.

(10) Patent No.: US 7,030,140 B2
(45) Date of Patent: Apr. 18, 2006

(54) SUBSTITUTED BENZIMIDAZOLE ANTIVIRAL AGENTS

(75) Inventors: Kuo-Long Yu, Hamden, CT (US); Rita Lee Civiello, Killingworth, CT (US); Mark R. Krystal, Westport, CT (US); Kathleen F. Kadow, Wallingford, CT (US); Nicholas A. Meanwell, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 122 days.

(21) Appl. No.: 10/934,921

(22) Filed: Sep. 3, 2004

(65) Prior Publication Data

US 2005/0038085 A1     Feb. 17, 2005

Related U.S. Application Data

(60) Division of application No. 10/289,829, filed on Nov. 7, 2002, now Pat. No. 6,908,936, which is a continuation of application No. 09/354,958, filed on Jul. 16, 1999, now abandoned.

(60) Provisional application No. 60/093,387, filed on Jul. 20, 1998.

(51) Int. Cl.
*A61K 31/4192* (2006.01)
*A61K 31/454* (2006.01)
*A61K 31/4439* (2006.01)

(52) U.S. Cl. ................. 514/322; 514/338; 514/359

(58) Field of Classification Search ............ 514/322, 514/338, 359
See application file for complete search history.

(56) References Cited

U.S. PATENT DOCUMENTS

| 3,394,141 | A | 7/1968 | Sparatore |
| 4,324,794 | A | 4/1982 | Tidwell et al. |
| 5,066,656 | A | 11/1991 | Greco et al. |
| 5,256,668 | A | 10/1993 | Hsu et al. |
| 2003/0207868 | A1* | 11/2003 | Yu et al. ............... 514/224.2 |

FOREIGN PATENT DOCUMENTS

| AU | 14704/97 | 8/1997 |
| EP | 0058146 A1 | 8/1982 |

OTHER PUBLICATIONS

"Update: Respiratory Syncytial Virus Activity-United States, 1996-97 Season," JAMA, vol. 277, No. 1, pp. 12-13, Jan. 1, 1997.
E. DeClercq, "Perspectives for the Chemotherapy of Respiratory Syncytial Virus (RSV) Infections," International Journal of Antimicrobial Agents, 7, pp. 193-202, 1996.
R. R. Tidwell, et al, "Aromatic Amidines: Comparison of Their Ability to Block Respiratory Syncytial Virus Induced Cell Fusion and to Inhibit Plasmin, Urokinase, Thrombin, and Trypsin," J. Med. Chem., 26, pp. 294-298, 1983.
E. J. Dubovi, et al, "Inhibition of Respiratory Syncytial Virus-Host Cell Interactions by Mono- and Diamidines," Antimicrobial Agents and Chemotherapy, vol. 19, No. 4, pp. 649-656, Apr., 1981.
P. R. Wyde, et al, "CL387626 Exhibits Marked and Unusual Antiviral Activity Against Respiratory Syncytial Virus in Tissue Culture and in Cotton Rats," Antiviral Research, 38, pp. 31-42, 1998.
F. Pagani, et al, "Benzotriazolil-Alchil-Benzimidazoli E Loro Derivati Dialchil-Amminoalchilici," Boll. Chim. Farm., 104, pp. 427-431, 1965.
G. Paglietti, et al, "Dialchilamminoalchilbenzimidazoli Di Interesse Farmacologico," Il Farmaco, Ed. Sci., vol. 30, pp. 505-511, 1975.
F. Sparatore, et al, " Dialchilamminoalchilbenzimidazoli D' Interesse Farmacologico," Il Farmaco, Ed. Sci., vol. 23, pp. 344-359, 1967.
S. Shigeta, et al, "Inhibitory Effect of Pyridobenzoazoles on Orthomyxo- and Paramyxovirus Replication In Vitro," Antiviral Chemistry and Chemotherapy, 3(3), 171-177, 1992.
W. R. Roderick, et al, "Bisbenzimidazoles. Potent Inhibitors of Rhinoviruses," Journal of Medicinal Chemistry, vol. 15, No. 6, pp. 655-658, 1972.
B. Cakir, et al, "Benzimidazole Derivatives: bis-Benzimidazoles and Their Antifungal Activities," Gazi Ecz. Fak. Der., 5(1), pp. 71-77, 1988.
F. Sparatore, et al, "Derivati Benzotriazolici Attivi Sull'accrescimento Delle Piante," Il Farmaco, Ed. Sci., 33, pp. 901-923, 1978.

(Continued)

*Primary Examiner*—Patricia L. Morris
(74) *Attorney, Agent, or Firm*—James Epperson

(57) ABSTRACT

The present invention concerns antiviral compounds, their compositions, and use in the treatment of viral infections. More particularly, the invention provides benzimidazole derivatives for the treatment of respiratory syncytial virus infection.

1 Claim, No Drawings

OTHER PUBLICATIONS

A. R. Katritzky, et al, "Syntheses and Transformations of Substituted Benzazolyl- and Tetrazolyl(Benzotriazol-1-yl) Methanes," J. Heterocyclic Chem., vol. 33, pp. 1107-1114, 1996.

T. A. Fairley, et al, "Structure, DNA Minor Groove Binding, and Base Pair Specificity of Alkyl- and Aryl- Linked Bis (Amidinobenzimidazoles) and Bis(Amidinoindoles)," J. Med. Chem., 36, pp. 1746-1753, 1993.

R. K. Upadhyay, et al, "New Heterocycles: Synthesis and Biological Evaluation," Indian Journal of Heterocyclic Chemistry, vol. 4, pp. 121-124, Oct.-Dec. 1994.

A. R. Katritzky, et al, "A New Route to N-Substituted Heterocycles," TETRAHEDRON, vol. 49, No. 14, pp. 2829-2838, 1993.

E. J. Dubovi, et al, "Inhibition of Respiratory Syncytial Virus by Bis-5-Amidino-2-Benzimidazolyl)Methane," VIROLOGY, 103, pp. 502-504, 1980.

* cited by examiner

SUBSTITUTED BENZIMIDAZOLE ANTIVIRAL AGENTS

This application is a divisional of application 10/289,829, filed Nov. 7, 2002, now U.S. Pat. No. 6,908,936, which is a continuation of U.S. application Ser. No. 09/354,958, filed Jul. 16, 1999, now abandoned, and claims priority to provisional application Ser. No. 60/093,387, filed Jul. 20, 1998.

BACKGROUND OF THE INVENTION

1. Field of the Invention

The present invention concerns antiviral compounds, their methods of preparation and their compositions, and use in the treatment of viral infections. More particularly, the invention provides benzimidazole derivatives for the treatment of respiratory syncytial virus infection.

2. Background Art

Respiratory syncytial virus (RSV) is the leading cause of serious lower respiratory tract infection in infants, children, elderly and immunocompromised persons. Severe infection of the virus may result in bronchiolitis or pneumonia which may require hospitalization or result in death. (*JAMA*, 1997, 277, 12). Currently only Ribavirin is approved for the treatment of this viral infection. Ribavirin is a nucleoside analogue which is administered intranasally as an aerosol. The agent is quite toxic, and its efficacy has remained controversial. RespiGam, approved for prophylaxis in high risk pediatric patients, is an intravenous immunoglobulin which effectively neutralizes the virus. Recently, Synagis, a monoclonal antibody administered through intramuscular injection has also been approved for use in high risk pediatric patients. However, both drugs are very expensive. Accordingly, inexpensive, safe and effective antiviral agents against respiratory syncytial virus will be beneficial for patients.

Many agents are known to inhibit respiratory syncytial virus (De Clercq, *Int. J. Antiviral Agents*, 1996, 7, 193). Y. Tao et al. (EP 0 058 146 A1, 1998) disclosed that Ceterizine, a known antihistamine, exhibited anti-RSV activity. Tidwell et al., *J. Med. Chem.* 1983, 26, 294 (U.S. Pat. No. 4,324,794, 1982), and Dubovi et al., *Antimicrobial Agents and Chemotherapy*, 1981, 19, 649, reported a series of amidino compounds with the formula shown below as inhibitors of RSV.

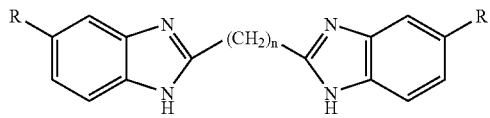

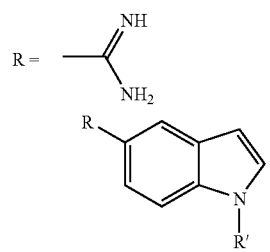

Hsu et al., U.S. Pat. No. 5,256,668 (1993) also disclosed a series of 6-aminopyrimidones that possess anti-viral activity against RSV.

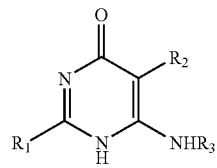

In addition, Y. Gluzman, et al., (AU Patent, Au-A-14,704, 1997) and P. R. Wyde et al. (*Antiviral Res.* 1998, 38, 31) disclosed a series of triazine containing compounds that were useful for the treatment and/or prevention of RSV infection.

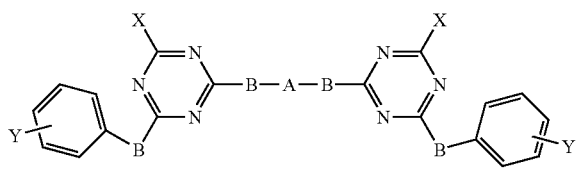

This invention relates to the antiviral activity against RSV found in a series of 1-Substituted 2-(benzotriazolylmethyl)-benzimidazoles. Some of the compounds in our invention were first disclosed by F. Pagani and F. Sparatore in *Boll Chim Farm.* 1965, 104, 427 and by G. Paglietti, et al. in *Il Farmaco, Ed. Sci.* 1975, 30, 505, and found to possess analgesic and anti-arrhythmic activity. The structural formula for these compounds are depicted in Formula Ia and Ib.

Formula Ia

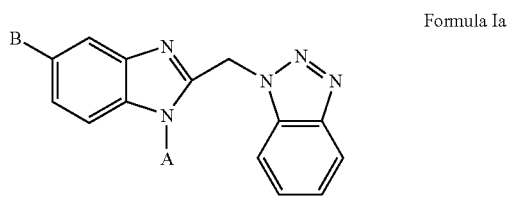

Formula Ib

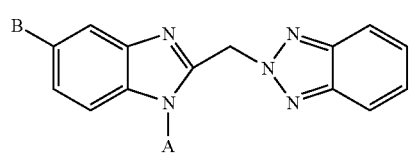

In Formula Ia and Ib, A is —(CH$_2$)n-N(R)$_2$, n=2 or 3, R=Me or Et, or A is

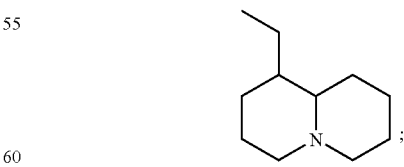

B=H, Cl, CF$_3$, CH$_3$CO, NO$_2$.

Another series of closely related compounds that Sparatore had disclosed were in *Il Farmaco Ed. Sci.* 1967, 23, 344 (U.S. Pat. No. 3,394,141, 1968). Some of the compounds were reported to have analgesic, anti-inflammatory or antipyretic activities. The structure of these compounds is depicted in formula Ic. In Formula Ic, C=H, CF₃, or NO₂. D is —(CH₂)n-NR₂, n=2 or 3, R=Me or Et, or

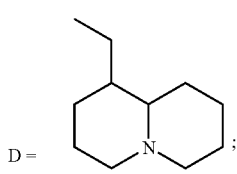

E is H, Cl or OEt.

Formula Ic

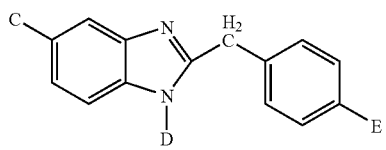

Another series of compounds structurally related to this invention are pyrido[1,2-a]benzoazoles and pyrimidio[1,2a] benzimidazoles disclosed by S. Shigeta et al in *Antiviral Chem. & Chemother.* 1992, 3, 171. These compounds have demonstrated inhibition of orthomyxovirus and paramyxovirus replication in HeLa cells. The structures of these compounds are shown in formulas Id and Ie, in which F=NH, S, or O; Q=—NHCOPh, —COOH, COOEt, or CN; T=COMe, CN, or COOEt; G=O or NH.

Formula Id

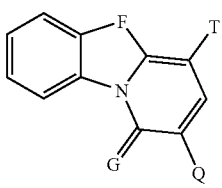

Formula Ie

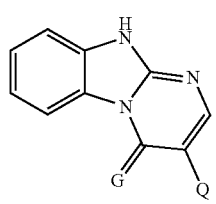

A bis-benzimidazole with an ethylenediol linker shown below has also been reported as a potent inhibitor of rhinoviruses (Roderick, et al. *J. Med. Chem.* 1972, 15, 655.

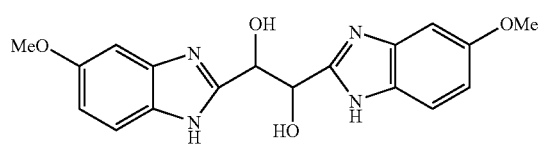

Other structurally related compounds are bis-benzimidazoles which possess antifungal activity (B. Cakir, et al. *Eczacilik Fak. Derg.* 1988, 5, 71.

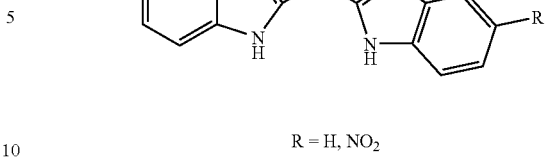

R = H, NO₂

Compounds of the present invention are benzimidazole derivatives and pharmaceutically acceptable salts thereof.

Other prior art related to the chemical structure of the present invention:

(1) F. Sparatore, et al, "Derivati Benzotriazolici Attivi Sull'accrescimento Delle Piante," *Il Farmaco Ed. Sci.* 1978, 33, 901.

(2) Katritzky, A. R. et al, "Synthesis and Transformations Of Substituted Benzazolyl- and Tetrazolyl(benzotriazol-1-yl) methanes," *J. Heterocyclic Chem.* 1996, 33, 1107.

(3) Terri A. Fairley, et al. "Structure, DNA Minor Groove Binding, And Base Pair Specificity of Alkyl and Aryl-Linked Bis(amidinobenzimidazoles) and Bis(amidinoindoles), *J. Med. Chem.* 1993, 36, 1746.

(4) R. K. Upadhyay et al, "New Synthesis and Biological Evaluation," *Indian J. Heterocyclic Chem.* 1994, 4, 121.

(5) A. R. Katrizky, et al, "A New Route to N-substituted Heterocycles," *Tetrahedron,* 1993, 49, 2829.

SUMMARY OF THE INVENTION

The present invention relates to compounds having the Formula II and Formula III Formula II

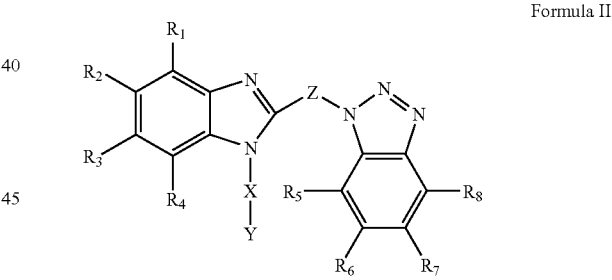

Formula III

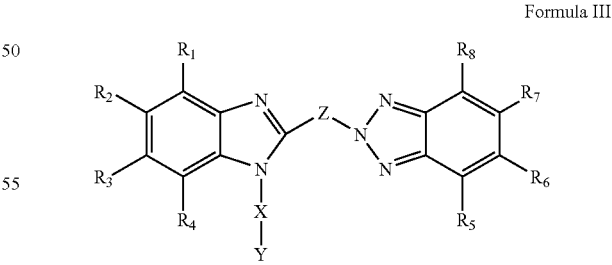

wherein:

$R_1$, $R_2$, $R_3$, $R_4$, $R_5$, $R_6$, $R_7$ and $R_8$ are independently H, alkyl, alkyl substituted with 1 to 6 halogen atoms, $NO_2$, CN, halogen, COR', COOR', and CONHR', R' is H or alkyl, and said alkyl contains 1 to 6 carbon atoms;

X is straight, branched or cyclic alkyl, alkenyl, and alkynyl groups, wherein said groups have 2 to 12 carbon atoms;

Y is selected from:
(a) $R_9$, —$NR_9R_{10}$, —$^+NR_9R_{10}R_{11}$, —$NHCOR_9$, =N—O—$R_9$; —$CONHR_9$, —$COOR_9$, —CO—$R_9$, —$OR_9$, wherein $R_9$, $R_{10}$ and $R_{11}$ are independently H, straight, branched or cyclic alkyl containing 1 to 7 carbon atoms; or $R_9$ taken together with $R_{10}$ forms a cyclic alkyl group having 3 to 7 carbon atoms;
(b) —$N_3$, —CN, halogen, —$NO_2$, —NR"$SO_2$R'", —SR", —SOR", —$SO_2$R", —$SO_2$NR",

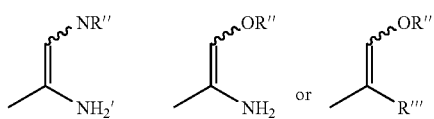

wherein said R" and R'" are independently hydrogen, $C_1$–$C_6$ alkyl, phenyl, or phenyl substituted with from 1 to 6 halogen atoms or $C_1$–$C_6$ alkyl groups;
(c) phenyl or heterocycle, selected from dioxolane, pyridine, pyrrole, thiophene, pyrrolidine or piperidine, and wherein said phenyl is optionally substituted with from 1 to 6 halogen atoms or $C_1$–$C_6$ alkyl groups;
or X and Y taken together is selected from —$CH_2Ph$, —$CH_2COPh$, —$CH_2CHOHPh$,

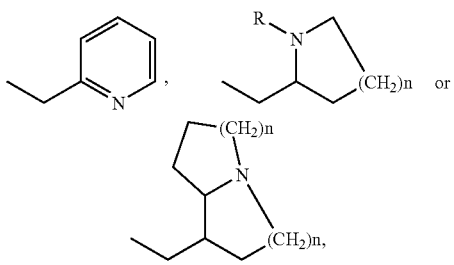

wherein n is 1 or 2, R is $C_1$–$C_4$ alkyl and Ph is phenyl;
Z is —$(CR_{12}R_{13})_n$—, wherein n is 1–4, and $R_{12}$ and $R_{13}$ are independently H, straight, branched or cyclic $C_1$–$C_6$ alkyl;
provided when $R_2$ is H, Cl, $CF_3$, $CH_3CO$ or $NO_2$; $R_1$, $R_3$, $R_4$, $R_5$, $R_6$, $R_7$ and $R_8$ are not at the same time H; Z is not $(CH_2)_n$, where n is 1–3; X is not $(CH_2)z$, where z is 2 or 3; Y is not $N(CH_3)_2$ or $N(C_2H_5)_2$ or X and Y taken together is not

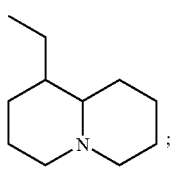

further provided when X and Y taken together is —$CH_2CH(CH_3)_2$, then Z is not $CH_2$ and $R_1$, $R_2$, $R_3$, $R_4$, $R_5$, $R_6$, $R_7$ and $R_8$ are not each H at the same time.

A preferred embodiment are those compounds wherein:
$R_1$, $R_3$, $R_4$, $R_5$, $R_6$, $R_7$ and $R_8$ are each H; $R_2$ is H, $C_1$–$C_3$ alkyl, $C_1$–$C_3$ alkyl substituted with 1 to 6 halogen atoms, $NO_2$, CN, halogen, COR', COOR', or CONHR', wherein R' is H or $C_1$–$C_3$ alkyl;
X is —$(CH_2)_2$— or —$(CH_2)_3$;
Y is selected from
(a) H, straight, branched or cyclic $C_1$–$C_7$ alkyl; —$NR_9R_{10}$, —$^+NR_9R_{10}R_{11}$, —$NHCOR_9$, —CO—$R_9$, —$OR_9$, wherein $R_9$ and $R_{10}$, are independently H, straight or branched $C_1$–$C_3$ alkyl; or $R_9$ taken together with $R_{10}$, forms a cyclic alkyl group having 5 to 7 carbon atoms;
(b) —$NHSO_2$R", —SR", —SOR", —$SO_2$R", wherein said R" is $C_1$–$C_3$ alkyl;
or X and Y taken together is selected from —$CH_2COPh$, —$CH_2CHOHPh$,

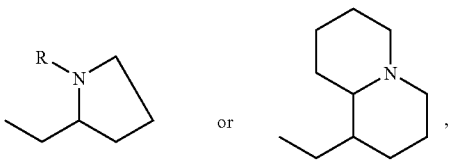

wherein R is $C_1$–$C_3$alkyl; and
Z is $CH_2$.

Another preferred embodiment are those compounds wherein:
$R_1$, $R_3$, $R_4$, $R_5$, $R_6$, $R_7$ and $R_8$ are each H; $R_2$ is H or halogen;
X is —$(CH_2)_2$— or —$(CH_2)_3$;
Y is selected from
(a) H, straight, branched or cyclic $C_1$–$C_7$ alkyl; —$NR_9R_{10}$, —$^+NR_9R_{10}R_{11}$, —CO—$R_9$, or —$OR_9$, wherein $R_9$ and $R_{10}$ are independently H, straight, branched $C_1$–$C_3$ alkyl; or $R_9$ taken together with $R_{10}$, forms a cyclic alkyl group having 5 to 7 carbon atoms;
(b) —SR", —SOR" or —$SO_2$R", wherein said R" is $CH_3$;
or X and Y taken together is —$CH_2COPh$ or —$CH_2CHOHPh$; and
Z is $CH_2$.

In another embodiment of the invention there is provided a method for treating mammals infected with RSV, and in need thereof, which comprises administering to said mammal a therapeutically effective amount of one or more of the aforementioned compounds having the Formula II or Formula III, including pharmaceutically acceptable salts thereof, but not subject to the proviso thereto.

Another embodiment includes a pharmaceutical composition which comprises a therapeutically effective amount of one or more of the aforementioned anti-RSV compounds having Formula II or Formula III, including pharmaceutically acceptable salts thereof, and a pharmaceutically acceptable carrier.

The term pharmaceutically aceptable salt includes solvates, hydrates, acid addition salts and quarternary salts. The acid addition salts are formed from a compound of Formula II or III compound and a pharmceutically acceptable inorganic acid including but not limited to hydrochloric, hydrobromic, sulfuric, phosphoric, methanesulfonic, acetic, citric, malonic, fumaric, maleic, sulfamic, or tartaric acids. Quaternary salts include chloride, bromide, iodide, sulfate, phosphate, methansulfonate, citrate, acetate, malonate, fumarate, sulfamate, and tartrate.

DETAILED DESCRIPTION OF THE INVENTION

Compounds of formula II and III may be prepared using the procedures described by F. Sparatore et al. in *Il Far-* maco-Ed. Sci. 1967, 23, 344, and by G. Paglietti, et al. in *Framco, Ed. Sci.* 1975, 30, 505.

Alternatively, compounds of formula II may be prepared from compound IV using the procedure described in Scheme I. The starting materials, however, are not particularly limited, and can be their substituted derivatives so long as there is a free NH at the 1-position of the benzimidazole moiety. Compound IV and its derivatives can be prepared from the corresponding derivatives of benzotriazol-1-yl-acetic acid and phenylenediamine using the procedures described by A. Katritzky et al. (*J. Heterocyclic Chem.* 1996, 33, 1107) or by W. Siegart and A. Day (*J. Am. Chem. Soc.* 1957, 79, 4391).

In Scheme IA, the starting material, compound of formula IV, is reacted with sodium hydride or potassium carbonate followed by the addition of the corresponding halides (RX) or alkylsulfonates (R-OMs) to produce compounds of formula II. The compound in Formula II can also be prepared by reacting IV with acrylates, acrylamides or vinyl alkyl ketones in the presence of 1,3,4,6,7,8-hexahydro-1-methyl-2H-pyrimido[1,2-a] pyrimidine (MTBD) or Triton-B, as shown in Scheme IB. The resulting amides or ketones can be reduced further by sodium borohydride, lithium aluminum hydride, or alane, to the corresponding amines or alcohols. In an alternative route (Scheme IC), the compound in Formula II can be prepared by reacting compound IV with alcohols in the presence of 1,1'-(azodicarbonyl)-dipiperidine (ADDP) and tributylphosphine, as shown in Scheme Ic.

In a different route shown in Scheme II, compound of Formula IV can be heated with ethylene carbonate to afford the alcohol of formula VI. Treatment of the alcohol with methanesulfonyl chloride and di-isopropylethylamine produces the compound of Formula VII. Displacement of the mesylate with sodium azide gave the azido compound of Formula VIII. Reduction of the azide provides the amine of Formula IX.

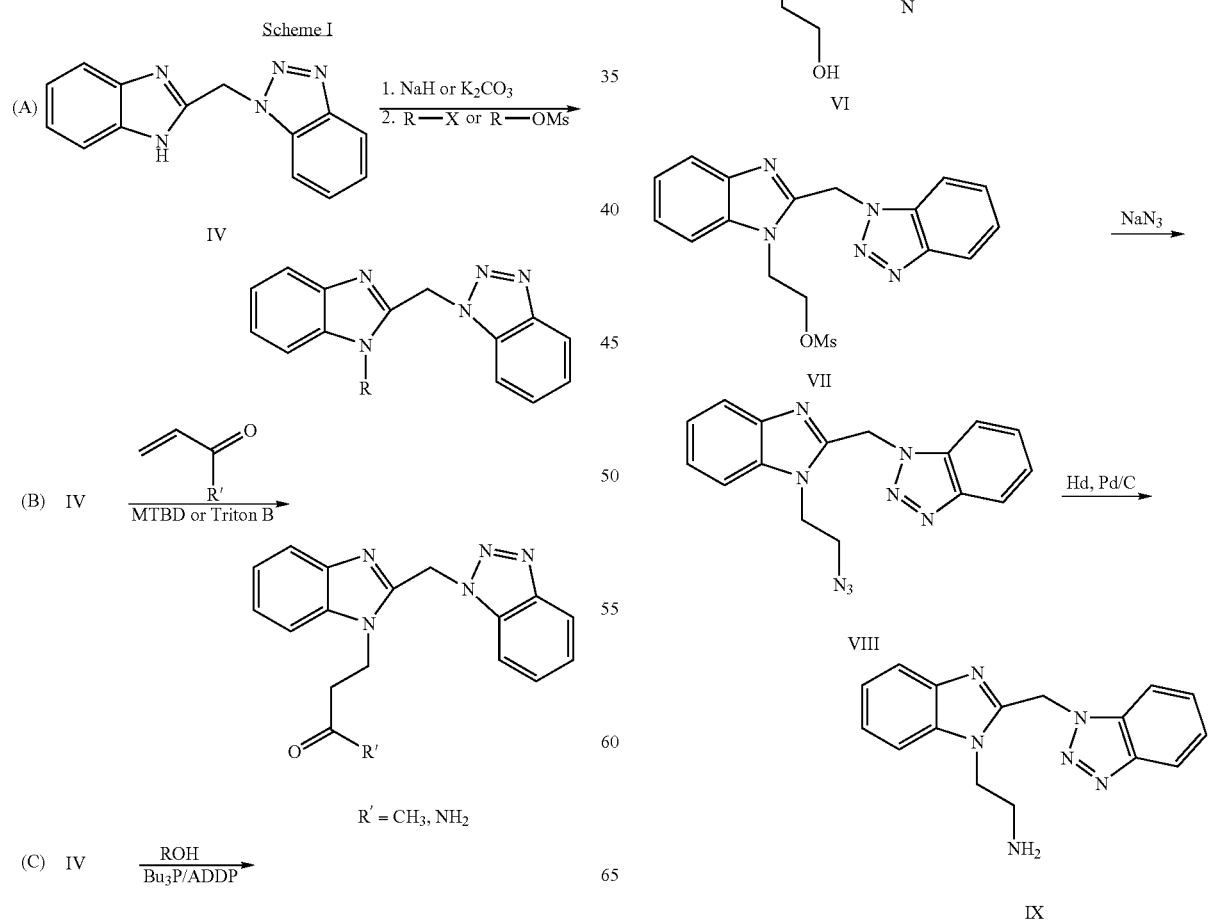

The compounds of Formula III can be prepared using the same procedure described in Scheme I-II using compound V or its substituted derivatives as the starting material. Compound V can be prepared using the procedure described in F. Pagani and F. Sparatore in *Boll Chim Farm.* 1965, 104, 427. Alternatively, the compound can be prepared using the reaction sequence depicted in Scheme III. In Scheme III, 2-chloromethylbenzimidazole reacts with methanesulfonyl chloride (MsCl) and triethylamine to give compound of Formula X. The chloride can be refluxed with potassium iodide in acetone to produce the compound of Formula XI. N-alkylation of benzotriazole with compound XI, followed by removal of the mesylate protecting group with hydrazine in methanol affords a 10:1 mixture of compounds of Formula IV and Formula V.

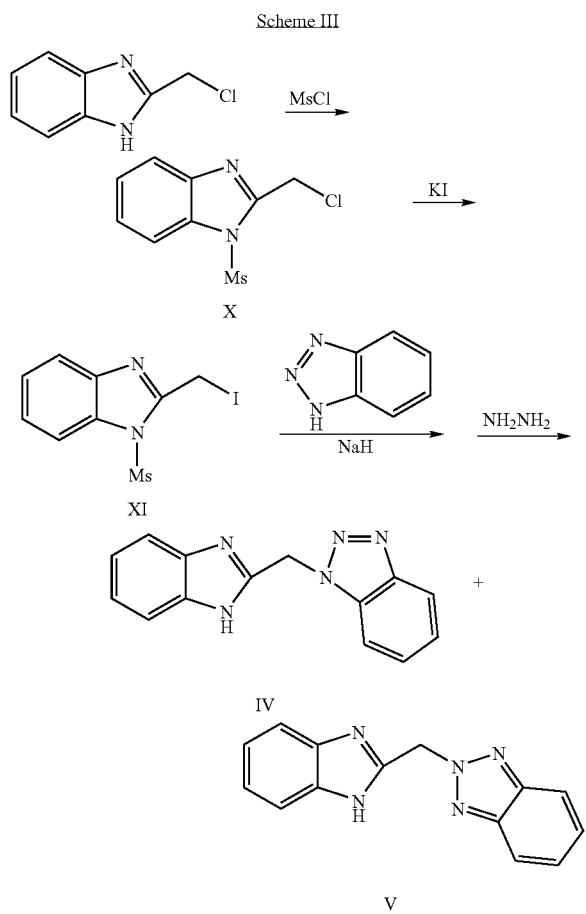

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

Treatment is preferably commenced before or at the time of infection and continued until virus is no longer present in the respiratory tract. However, the treatment can also be commenced when given post-infection, for example after the appearance of established symptoms.

Suitable treatment is given 1–4 times daily and continued for 3–7, e.g. 5 days post infection depending upon the particular compound used.

The desired dose may be presented in a single dose or as divided doses administered at appropriate intervals, for example as two, three, four or more sub-doses per day.

The compound is conveniently administered in unit dosage form, for example, containing 10 to 1500 mg, conveniently 20 to 1000 mg, most conveniently 50 to 700 mg of active ingredient per unit dosage form.

While it is possible that, for use in therapy, a compound of the invention may be administered as the raw chemical, it is preferable to present the active ingredient as a pharmaceutical formulation.

The invention thus further provides a pharmaceutical formulation comprising a compound of the formula II or formula III, but not subject to the proviso thereto, or a pharmaceutically acceptable salt or derivative thereof together with a pharmaceutically acceptable carrier thereof.

The carrier must be "acceptable" in the sense of being compatible with the other ingredients of the formulation and not deleterious to the recipient thereof.

The pharmaceutical formulations may be in the form of conventional formulations for the intended mode of administration.

For intranasal administration according to the method of the invention the compounds of the invention may be administered by any of the methods and formulations employed in the art for intranasal administration.

Thus in general the compounds may be administered in the form of a solution or a suspension or as a dry powder.

Solutions and suspensions will generally be aqueous, for example prepared from water alone (for example sterile or pyrogen-free water), or water and a physiologically acceptable co-solvent (for example ethanol, propylene glycol, and polyethylene glycols such as PEG 400).

Such solutions or suspensions may additionally contain other excipients, for example, preservatives (such as benzalkonium chloride), solubilizing agents/surfactants such as polysorbates (e.g. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomizing spray pump.

Intranasal administration may also be achieved by means of an aerosol formulation in which the compound is provided in a pressurized pack with a suitable propellant such as a chlorofluorocarbon (CFC), for example dichlorodifluoromethane, trichlorofluoromethane or dichlorotetrafluroroethane, carbon dioxide or other suitable gas. The aerosol may conveniently also contain a surfactant such as lecithin. The dose of drug may be controlled by provision of a metered valve.

Experimental Section Proton nuclear magnetic resonance ($^1$H NMR) spectra were recorded on a Bruker AC-300, Bruker DPX-300 or a Varian Gemini 300 spectrometer. All spectra were determined in CDCl$_3$, CD$_3$OD, or DMSO-d$_6$ and chemical shifts are reported in δ units relative to tetramethylsilane (TMS). Splitting patterns are designated as follows: s, singlet; d, doublet; t, triplet; m, multiplet; b, broad peak; dd, doublet of doublets. Mass spectroscopy were performed on a Finnegan SSQ 7000 quadrupole mass spectrometer in both positive and negative electrospray ionization (ESI) modes, or on a Finnegan TSQ 700 triple quadrupole mass spectrometer in positive direct chemical ionization (DCI) mode with isobutane as reagent gas. Infrared (IR) spectra were recorded on a Perkin-Elmer Model 2000 FTIR. Column chromatography was performed on silica gel from EM Science.

The synthesis of compounds in examples 1–4 and 51–53 was reported by F. Pagani et al. in *Boll Chim Farm.* 1965, 104, 427. Preparation of compounds in examples 5–8 and 54–56 was described by G. Paglietti, et al. in *Il Farmaco, Ed. Sci.* 1975, 30, 505. Preparation of compounds in examples 9–50 and 57–61 is described as follows:

Synthesis of Intermediate 1-(1H-Benzimidazol-2-ylmethyl)-1H-benzotriazole and 2-(1H-Benzimidazol-2-ylmethyl)-2H-benzotriazole

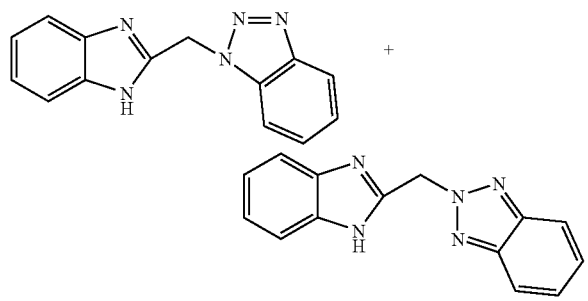

2-(Chloromethyl)-1-(methanesulfonyl)-benzimidazole

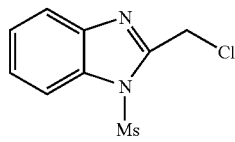

To a solution of 2-(Chloromethyl)benzimidazole (80 g, 0.48 mol) and methanesulfonyl chloride (58.3 mL, 0.75 mol) in 0.5 L of methylene chloride, triethylamine (136 mL, 0.97 mol) was added dropwise under nitrogen. The resulting mixture was stirred at room temperature for 6 hours. The mixture was filtered and the filtrate was evaporated. The residue was triturated in methanol and filtered to afford 74.9 g of the title compound as a brown solid.

IR (KBr, cm$^{-1}$): 3027, 2920, 1371, 1349, 1177, 1144, 1059.

$^1$H NMR (CDCl$_3$) δ 3.44 (s, 3H), 5.11 (s, 2H), 7.40–7.49 (m, 2H), 7.76–7.82 (m, 1H), 7.85–7.91 (m, 1H). MS m/e 245 (MH$^+$).

| Anal. Calcd for C$_9$H$_9$ClN$_2$O$_2$S: | C, 44.18; H, 3.71; N, 11.45. |
|---|---|
| Found: | C, 44.09; H, 3.57; N, 11.49. |

2-(Iodomethyl)-1-(methanesulfonyl)benzimidazole

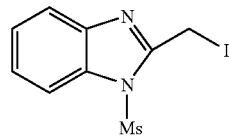

A solution of potassium iodide (206 g, 1.24 mol) and methanesulfonyl-2-Chloromethyl benzimidazole (74.8 g, 0.414 mol) in 1 L of acetone was stirred at reflux under nitrogen for 4 hours. The solid was filtered and the filtrate was evaporated. The crude product was triturated in methanol and filtered to give 83 g of the title compound as a solid.

IR (KBr, cm$^-$): 3022, 2916, 1366, 1173, 1055, 966, 763, 745.

$^1$H NMR (CDCl$_3$) δ 3.48 (s, 3H), 4.97 (s, 2H), 7.40–7.50 (m, 2H), 7.75–7.85 (m, 2H).

MS m/e 336 (MH$^+$).

| Anal. Calcd for C$_9$H$_9$IN$_2$O$_2$S: | C, 32.16; H, 2.70; N, 8.33. |
|---|---|
| Found: | C, 32.05; H, 2.63; N, 8.22. |

Benzotriazole (238 mg, 2 mmol) in 4 mL of anhydrous N,N-dimethylformamide was added sodium hydride (60% in mineral oil, 88 mg, 2.2 mmol). After stirring for 1 hour, 2-iodomethyl-1-methanesulfonyl benzimidazole (740 mg, 2.2 mmol) was added. The resulting solution was stirred for 6 hours, diluted with water, and extracted with diethyl ether. The combined extracts were dried over magnesium sulfate, and evaporated. To the residue was added 5 mL of methanol and hydrazine (0.5 mL), and stirred at 65° C. overnight. The solvent was evaporated and the residue was diluted with water and extracted with ethyl acetate. The combined extracts were dried over magnesium sulfate, and evaporated. The residue was purified by flash chromatography (EtOAc:hexane=1:1 to 2:1) to give 24 mg (5%) of 2-(1H-benzimidazol-2-ylmethyl)-2H-benzotriazole (IV), and 240 mg (48%) of 1-(1-benzimidazol-2-ylmethyl)-1H-benzotriazole (III) as solids.

1-(1-Benzimidazol-2-ylmethyl)-1H-benzotriazole:

IR (KBr, cm$^{-1}$): 3140, 3057, 1452, 1441, 1272, 1229, 1099, 734.

$^1$H NMR (CDCl$_3$) δ 6.23 (s, 2H), 7.28–7.31 (m, 3H), 7.46 (bt, J=7.3 Hz, 1H), 7.60–7.64 (m, 2H), 7.67 (d, J=8.3 Hz, 1H), 7.85 (d, J=7.8 Hz, 1H).

MS m/e 250 (MH$^+$).

| Anal. Calcd for C$_{14}$H$_{11}$N$_5$: | C, 67.46; H, 4.45; N, 28.09. |
|---|---|
| Found: | C, 67.34; H, 4.57; N, 28.17. |

2-(1-Benzimidazol-2-ylmethyl)-2H-benzotriazole

IR (KBr, cm$^{-1}$): 1435, 1324, 1274, 855, 739.

$^1$H NMR (CDCl$_3$) δ 6.26 (s, 2H), 7.25–7.31 (m, 2H), 7.38–7.42 (m, 2H), 7.59–7.61 (m, 2H), 7.83–7.88 (m, 2H).

MS m/e 250 (MH$^+$).

| | |
|---|---|
| Anal. Calcd for C$_{14}$H$_{11}$N$_5$: | C, 67.46; H, 4.45; N, 28.09. |
| Found: | C, 67.19; H, 4.54; N, 28.03. |

General Procedure For Coupling of 1-(1-Benzimidazol-2-ylmethyl)-1H-benzotriazole to Alkyl Halides:

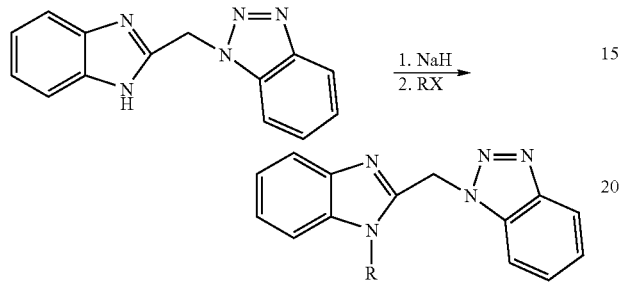

To 1-(1H-Benzimidazol-2-ylmethyl)-1H-benzotriazole (50 mg, 0.20 mmol) in 1.5 mL of solvent such as N,N-dimethylformamide, tetrahydrofuran, toluene or a mixture of solvents above, was added sodium hydride (60% suspension in mineral oil, 9 mg, 0.22 mmol) under nitrogen. After stirring for 30 minutes, the alkylhalide (0.22 mmol) was added. The reaction mixture was stirred overnight under nitrogen at a temperature ranging from 20° C. to 100° C. The reaction mixture was diluted with saturated aqueous sodium bicarbonate solution and extracted with diethyl ether or ethyl acetate. The extracts were dried over magnesium sulfate, filtered, and evaporated. The crude product was purified by flash chromatography on silica gel using a mixture of solvents such as hexane, ethyl acetate, methylene chloride and methanol. The pure product obtained can also be converted to a salt such as the hydrogen chloride salt by treating the compound in methanol with excess 4 N HCl in dioxane and evaporating. The procedure was repeated two times and the residue was triturated with ether, and filtered to afford the salt.

EXAMPLE 1

1-[1-(N,N-Dimethyl-aminoethyl)-1H-benzimidazol-2-ylmethyl]-1H-benzotriazole Hydrochloride

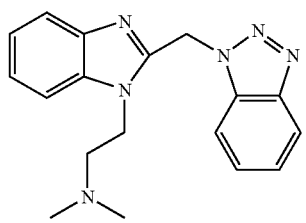

The general coupling procedure was applied using 2-dimethylaminoethyl chloride hydrochloride and sodium hydride in tetrahydrofuran to give the title compound in 23% yield:
IR (KBr, cm$^{-1}$): 3446, 3383, 2697, 1613, 1466, 1457, 773, 753.

$^1$H NMR (CD$_3$OD) δ 3.14 (s, 6H), 3.75–3.80 (m, 2H), 5.24–5.29 (m, 2H), 6.80 (bs, 2H), 7.53–7.79 (m, 5H), 8.07–8.14 (m, 3H).
MS m/e 320 (MH$^+$).

| | |
|---|---|
| Anal. Calcd for C$_{18}$H$_{20}$N$_6$·2HCl: | C, 54.69; H, 6.12; N, 21.26; Cl, 17.94 |
| Found: | C, 54.49; H, 5.81; N, 21.20; Cl, 17.71. |

EXAMPLE 9

2-[2-(1H-Benzotriazol-1-ylmethyl)-1H-benzimidazol-1-yl]-ethyl trimethylammonium iodide

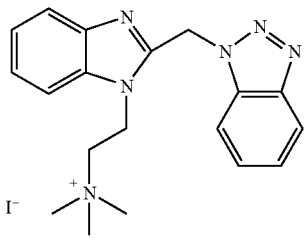

The free base of 1-[1-(N,N-dimethyl-aminoethyl)-1-benzimidazol-2-ylmethyl]-1H-benzotriazole (100 mg, 0.312 mmol) was dissolved in anhydrous acetone. Methyl iodide (44 mg, 0.312 mmol) was added with stirring under N$_2$ at room temperature. After 3 hours, the white solid was filtered and dried under vacuum to give 19.5 mg (14%) of the title compound as a white solid.
IR (KBr, cm$^{-1}$): 3000, 1615, 1469, 1458, 740.
$^1$H NMR (CD$_3$OD) δ 3.41(s, 9H), 3.62–3.68 (m, 2H), 5.05–5.11 (m, 2H), 6.43 (s, 2H), 7.35–7.52 (m, 3H), 7.60–7.72 (m, 3H), 7.98 (bd, J=7.5 Hz, 1H), 8.05 (bd, J=7.5 Hz, 1H).
MS m/e 335 (M-I$^+$).

| | |
|---|---|
| Anal. Calcd for C$_{19}$H$_{23}$IN$_6$: | C, 49.36; H, 5.01; N, 18.18. |
| Found: | C, 49.60; H, 4.86; N, 18.37. |

EXAMPLE 10

[2-(2-Benzotriazol-1-ylmethyl-benzimidazol-1-yl)-ethyl]-diisopropylamine Dihydrochloride

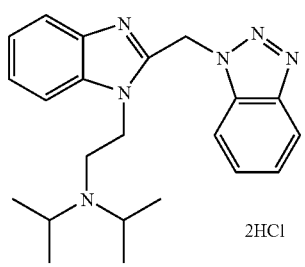

The general coupling procedure was applied using 2-di-isopropylaminoethyl chloride hydrochloride and sodium hydride in tetrahydrofuran to give the title compound in 51% yield:

IR (KBr, cm$^{-1}$): 2914, 2649, 1614, 1465, 1356, 779, 747.

$^1$H NMR (CD$_3$OD) δ 1.51 (d, J=6.5 Hz, 6H), 1.56 (d, J=6.5 Hz, 6H), 3.72 (m, 1H), 3.95–4.04 (m, 2H), 5.37–5.43 (m, 2H), 6.80 (s, 2H), 7.52–7.81 (m, 5H), 8.08–8.16 (m, 3H).

MS m/e 377 (MH$^+$).

EXAMPLE 11

[2-(2-Benzotriazol-1-ylmethyl-5,6-dimethyl-benzimidazol-1-yl]-ethyl]-dimethyl-amine

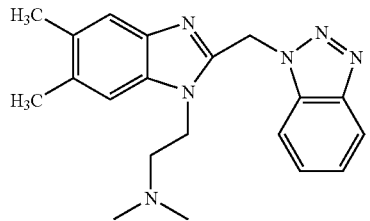

1-(5,6-Dimethyl-1H-benzimidazol-2-ylmethyl)-1H-benzotriazole

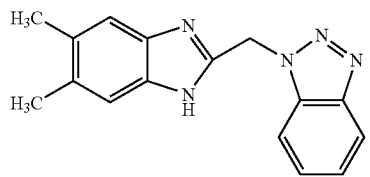

4,5-Dimethyl-1,2-phenylenediamine (0.77 g, 5.64 mmol) and 2-(1H-benzotriazol-1-yl)-acetic acid (1.0 g, 5.64 mmol) in polyphosphoric acid (1.3 g) at 175° C. was stirred for 2 hours. The reaction residue was added water and neutralized with sodium bicarbonate, and extracted with chloroform. The combined extracts were dried over magnesium sulfate and evaporated. The residue was triturated in hot ethyl acetate and filtered to give 564 mg of the product as a pale solid. The mother liquid was evaporated, and the residue was triturated in ether to give an additional 672 mg of the product.

IR (KBr, cm$^{-1}$): 1448, 1164, 1108, 744.

$^1$H NMR (DMSO-d$_6$) δ 2.25 (s, 6H), 6.15 (s, 2H), 7.20 (bs, 1H), 7.30 (bs, 1H), 7.36 (bt, J=8.4 Hz, 1H), 7.45 (bt, J=8.4 Hz, 1H), 7.67 (d, J=8.4 Hz, 1H), 8.05 (d, J=8.4 Hz, 1H).

MS m/e 278 (MH$^+$).

| Anal. Calcd for C$_{16}$H$_{15}$N$_5$: | C, 69.30; H, 5.45; N, 25.25. |
| Found: | C, 69.09; H, 5.41; N, 25.16. |

The general coupling procedure was applied using 1-(5,6-dimethyl-1H-benzimidazol-2-ylmethyl)-1H-benzotriazole, 2-dimethylaminoethyl chloride hydrochloride and sodium hydride in N,N-dimethylformamide in 75% yield to give the title compound:

IR (neat, cm$^-$): 3435, 2949, 2769, 1456, 1445, 1225, 745.

$^1$H NMR (CDCl$_3$) δ 2.56 (s, 6H), 2.33 (t, J=5.9 Hz, 2H), 2.35 (s, 6H), 4.23 (s, 2H), 7.09 (s, 1H), 7.29–7.41 (m, 2H), 7.56 (s, 1H), 7.74 (d, J=8.2 Hz, 1H), 8.01 (d, J=8.2 Hz, 1H).

MS m/e 349 (MH$^+$).

| Anal. Calcd for C$_{20}$H$_{24}$N$_6$.0.125H$_2$O: | C, 68.50; H, 6.97; N, 23.96. |
| Found: | C, 68.28; H, 7.07; N, 24.12. |

EXAMPLE 12

[2-(2-Benzotriazol-1-ylmethyl-5,6-dichloro-benzimidazol-1-yl]-ethyl]-dimethyl-amine

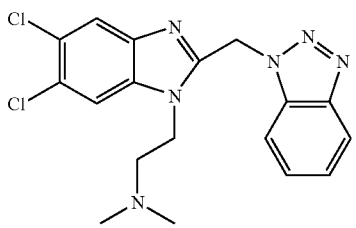

1-(5,6-Dichloro-1H-benzimidazol-2-ylmethyl)-5,6-1H-benzotriazole

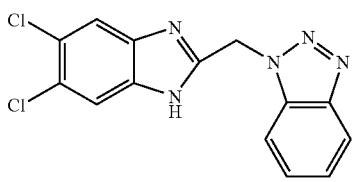

2-(1H-benzotriazol-1-yl)-acetic acid (1.0 g, 5.64 mmol) and 4,5-dichloro-1,2-phenylenediamine (1.0 g, 5.64 mmol) in 4 N HCl (40 mL) were stirred at reflux overnight. The solution was cooled to room temperature and neutralized with sodium bicarbonate. The mixture was extracted with tetrahydrofuran. The combined extracts were washed with brine, dried over magnesium sulfate, and evaporated. The residue was purified by flash chromatography (EtOAc:hexane=1:1 to straight EtOAc, gradient) to give a product which was triturated in ethyl acetate to give 425 mg of the product as a pink solid.

IR (KBr, cm$^{-1}$): 3128, 1443, 1309, 1096, 747.

$^1$H NMR (DMSO-d$_6$) δ 6.28 (s, 2H), 7.44 (t, J=6.9 Hz, 1H), 7.58 (t, J=6.9 Hz, 1H), 7.77 (s, 1H), 7.85 (s, 1H), 7.88 (d, J=8.3 Hz, 1H), 8.10 (d, J=8.3 Hz, 1H).

MS m/e 316 (M-H$^-$).

The general coupling procedure was applied using 1-(5,6-dichloro-1H-benzimidazol-2-ylmethyl)-5,6-1H-benzotriazole and 2-dimethylaminoethyl chloride hydrochloride in the presence of sodium hydride in N,N-dimethylformamide to give the title compound in 36% yield:

IR (KBr, cm$^{-1}$): 3436, 2787, 1464, 1446, 1080, 748.
$^1$H NMR (CDCl$_3$) δ 2.32 (s, 6H), 2.45 (t, J=6.1 Hz, 2H), 4.31 (bs, 2H), 6.26 (s, 2H), 7.36–7.50 (m, 3H), 7.77 (d, J=8.3 Hz, 1H), 7.91 (s, 1H), 8.07 (d, J=8.3 Hz, 1H).
MS m/e 389 (MH$^+$).

| Anal. Calcd for C$_{18}$H$_{18}$Cl$_2$N$_6$: | C, 55.54; H, 4.66; N, 21.59. |
|---|---|
| Found: | C, 55.51; H, 4.84; N, 21.36. |

EXAMPLE 13

{2-[2-(5,6-Dimethylbenzotriazol-1-ylmethyl)-benzimidazol-1-yl]-ethyl}-dimethyl-amine

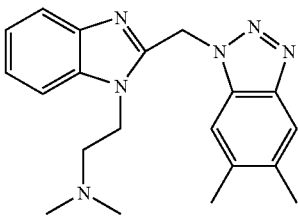

1-(1H-Benzimidazol-2-ylmethyl)-5,6-1H-benzotriazole

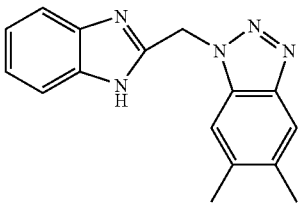

The same procedure described in the preparation of 1-(1H-benzimidazol-2-ylmethyl)-1H-benzotriazole was used, except that 5,6-dimethylbenzotriazole was used instead of benzotriazole. 1-(1H-benzimidazol-2-ylmethyl)-5,6-dimethyl-1H-benzotriazole was isolated as an intermediate:
IR (KBr, cm$^{-1}$): 3433, 2944, 1624, 1587, 1421, 1221.
$^1$H NMR (CDCl$_3$) δ 2.32 (s, 3H), 2.34 (s, 3H), 6.10 (s, 2H), 7.24–7.28 (m, 2H), 7.37 (s, 1H), 7.58 (bs, 2H), 7.63 (s, 1H).
MS m/e 278 (MH$^+$).
The general coupling procedure was applied using 1-(1H-benzimidazol-2-ylmethyl)-5,6-dimethyl-1H-benzotriazole and 2-dimethylaminoethyl chloride hydrochloride in the presence of sodium hydride in N,N-dimethylformaide to give the title compound in 11% yield:
IR (neat, cm$^{-1}$): 3404, 2949, 2466, 1625, 1463, 751. $^1$H NMR (CD$_3$OD) δ 2.43 (s, 3H), 2.49 (s, 3H), 3.11 (s, 6H), 3.58–3.64 (m, 2H), 5.13–5.19 (m, 2H), 6.59 (s, 2H), 7.55–7.66 (m, 2H), 7.76 (d, J=7.7 Hz, 1H), 7.82 (d, 1H), 7.83 (d, J=6.6 Hz, 1H), 7.98 (d, J=8.0 Hz, 1H).
MS m/e 349 (MH$^+$).

EXAMPLE 14

1-[1-(2-Pyrrolidin-1-yl-ethyl)-1H-benzimidazol-2-ylmethyl)]-1H-benzotriazole Dihydrochloride

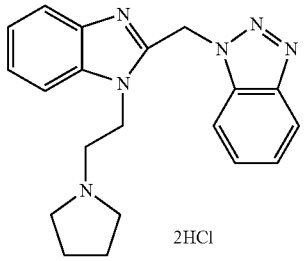

The general coupling procedure was applied using 1-(2-chloroethyl)-pyrrolidine hydrochloride and sodium hydride in tetrahydrofuran to give the title compound in 38% yield:
IR(KBr, cm$^{-1}$): 3412, 2929, 2465, 1800, 1615, 1520, 1457.
$^1$H NMR (CD$_3$OD) δ 2.13–2.26 (m, 4H), 3.64–3.85 (m, 6H), 5.05–5.11 (m, 2H), 6.59 (s, 2H), 7.49–7.76 (m, 5H), 7.89 (d, J=7.9 Hz, 1H), 8.02 (d, J=8.4 Hz, 1H), 8.09 (d, J=8.7 Hz, 1H).
MS m/e 347 (MH$^+$).

EXAMPLE 15

1-(2-Piperidin-1-yl-ethyl)-1H-benzimidazol-2-ylmethyl)-1H-benzotriazole Dihydrochloride

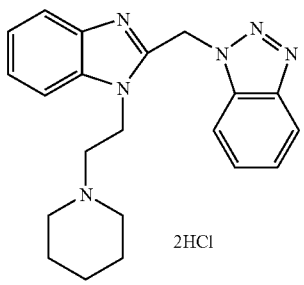

The general coupling procedure was applied using 1-(2-chloroethyl)-piperidine hydrochloride and sodium hydride in tetrahydrofuran to give the title compound in 10% yield:
$^1$H NMR (CD$_3$OD) δ 1.95–2.15 (m, 6H), 3.10–3.20 (m, 2H), 3.50–3.80 (m, 4H), 5.10–5.20 (m, 2H), 6.62 (bs, 2H), 7.50–7.76 (m, 5H), 7.93 (d, J=8.0 Hz, 1H), 8.02 (d, J=8.4 Hz, 1H), 8.10 (d, J=8.4 Hz, 1H).
MS m/e 361 (MH$^+$).

EXAMPLE 16

1-(2-Azepin-1-yl-ethyl)-1H-benzimidazol-2-ylmethyl)-1H-benzotriazole Dihydrochloride

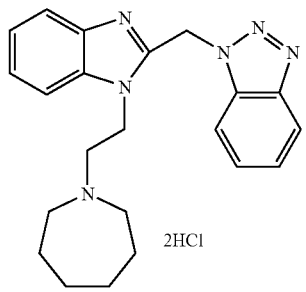

The general coupling procedure was applied using 2-(hexamethyleneimino)ethyl chloride hydrochloride and sodium hydride in tetrahydrofuran to give the title compound in 27% yield:

IR(KBr, cm$^{-1}$): 3430, 2928, 2472, 1727, 1455, 1362.

$^1$H NMR (CD$_3$OD) δ 1.82 (bs, 4H), 2.04 (bs, 4H), 3.42–3.44 (m, 2H), 3.56–3.74 (m, 4H), 5.18–5.23 (m, 2H), 6.67 (s, 2H), 7.52–7.77 (m, 5H), 8.00 (d, J=8.4 Hz, 1H), 8.04 (d, J=8.4 Hz, 1H), 8.11 (d, J=8.4 Hz, 1H).

MS m/e 375 (MH$^+$).

| Anal. Calcd. for C$_{22}$H$_{26}$N$_6$.2HCl.H$_2$O: | C, 56.16; H, 7.23; N, 13.10 |
|---|---|
| Found: | C, 56.28; H, 6.86; N, 13.27. |

EXAMPLE 17

(S)-1-[1-Methyl-2-pyrrolidin-2-yl-methyl]-1H-benzimidazol-2-ylmethyl]-1H-benzotriazole Dihydrochloride

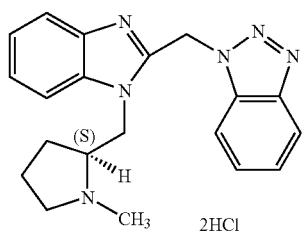

The required (S)-2-(Chloromethyl)-1-methylpyrrolidine hydrochloride was prepared according to the procedure reported by S. D. Kimball et al, *J. Med. Chem.* 1992, 35, 780–793. The general coupling procedure was applied using sodium hydride as a base in N,N-dimethylformamide to give the title compound as a dihydrochloride salt (17% yield):

$^1$H NMR (CD$_3$OD) δ 2.00–2.30 (m, 4H), 3.29 (s, 3H), 3.56–3.90 (m, 2H), 4.20–4.30 (m, 1H), 5.10 (dd, J=9.3, 15.1 Hz, 1H), 5.30 (dd, J=5.7, 15.1 Hz, 1H), 6.76 (bs, 2H), 7.52–7.77 (m, 6H), 8.01–8.13 (m, 2H).

MS m/e 347 (MH$^+$).

EXAMPLE 18

(R)-1-[1-Methyl-2-pyrrolidin-2-yl-methyl]-1H-benzimidazol-2-ylmethyl]-1H-benzotriazole

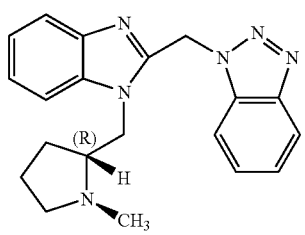

The required starting material (R)-2-(Chloromethyl)-1-methylpyrrolidine hydrochloride was prepared according to the procedure reported by S. D. Kimball et al, *J. Med. Chem.* 1992, 35, 780–793 using (R)-N-methyl proline methyl ester (N.-H. Lin, et al. U.S. Pat. No. 5,424,444, 1995). The general coupling procedure was applied using sodium hydride as a base in N,N-dimethylformamide to give the title compound in 23% yield:

IR (KBr, cm$^{-1}$): 2941, 2795, 1613, 1463, 1227, 755.

$^1$H NMR (CDCl$_3$) δ 1.50–1.59 (m, 1H), 1.59–1.86 (m, 3H), 1.96 (s, 3H), 2.18–2.20 (m, 1H), 2.65–2.74 (m, 1H), 2.90–3.05 (m, 1H), 4.06–4.23 (m, 2H), 6.18 (d, J=15.3 Hz, 1H), 7.20–7.38 (m, 5H), 7.72–7.76 (m, 2H), 7.96 (d, J=8.3 Hz, 1H).

MS m/e 347 (MH$^+$).

| Anal. Calcd for C$_{20}$H$_{22}$N$_6$: | C, 69.34; H, 6.40; N, 24.26 |
|---|---|
| Found: | C, 68.99; H, 6.49; N, 24.13. |

EXAMPLE 19

1-(1-Butyl-1H-benzimidazol-2-ylmethyl)-1H-benzotriazole

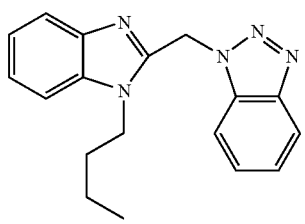

The general coupling procedure was applied using 1-bromobutane and sodium hydride in N,N-dimethylformamide to give the title compound in 61% yield:

IR (KBr, cm$^{-1}$): 2957, 1471, 1440, 1328, 1230, 735.

$^1$H NMR (CDCl$_3$) δ 0.85 (t, J=7.1 Hz, 3H), 1.21–1.43 (m, 4H), 4.20 (t, J=7.1 Hz, 2H), 6.18 (s, 2H), 7.25–7.44 (m, 5H), 7.75–7.83 (m, 2H), 8.02 (d, J=8.3 Hz, 1H).

MS m/e 306 (MH$^+$).

EXAMPLE 20

1-[1-(3-Methylbutyl)-1H-benzimidazol-2-ylmethyl)-1H-benzotriazole

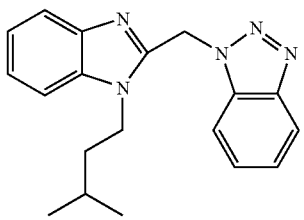

The general coupling procedure was applied using 1-bromo-3-methylbutane and sodium hydride in N,N-dimethylformamide to give the title compound in 74% yield:

IR (KBr, cm$^{-1}$): 1474, 1453, 1091, 752, 736.

$^1$H NMR (CDCl$_3$) δ 0.91 (d, J=6.6 Hz, 6H), 1.17–1.25 (m, 2H); 1.57–1.70 (m, 1H), 4.19–4.24 (m, 2H), 6.20 (s, 2H), 7.25–7.45 (m, 5H), 7.76–7.84 (m, 2H), 8.03 (d, J=8.0 Hz, 1H).

MS m/e 320 (MH$^+$).

| Anal. Calcd for C$_{19}$H$_{21}$N$_5$: | C, 71.45; H, 6.63; N, 21.93. |
|---|---|
| Found: | C, 71.35; H, 6.72; N, 21.92. |

EXAMPLE 21

1-[1-(3-Methyl-2-butenyl)-1H-benzimidazol-2-ylmethyl]-1H-benzotriazole

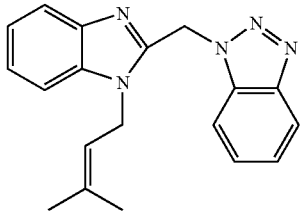

The general coupling procedure was applied using 1-bromo-3-methyl-2-butene and sodium hydride in tetrahydrofuran to give the title compound in 54% yield:

IR(KBr, cm$^{-1}$): 2930, 1614, 1464, 1418, 1086, 751.

$^1$H NMR (CDCl$_3$) δ 1.58 (bs, 6H), 4.75–4.73 (m, 1H), 4.83–4.85 (m, 2H), 6.18 (s, 2H), 7.25–7.44 (m, 5H), 7.73–7.82 (m, 2H), 8.01 (d, J=8.2 Hz, 1H),

MS m/e 318 (MH$^+$).

| Anal. Calcd for C$_{19}$H$_{19}$N$_5$.0.1H$_2$O: | C, 71.49; H, 6.06; N, 21.94 |
|---|---|
| Found: | C, 71.39; H, 6.20; N, 21.70 |

EXAMPLE 22

1-[1-(4-Methylpentyl)-1H-benzimidazol-2-ylmethyl]-1H-benzotriazole

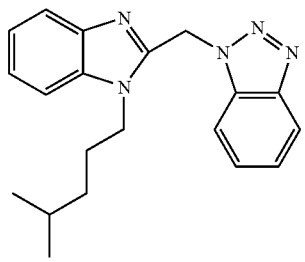

The general coupling procedure was applied using 1-bromo-4-methylpentane and sodium hydride in tetrahydrofuran to give the title compound in 80% yield:

IR (KBr, cm$^{-1}$): 2956, 1475, 1457, 1087, 751, 736.

$^1$H NMR (CDCl$_3$) δ 0.98 (s, 9H), 1.17–1.25 (m, 2H), 4.20–4.25 (m, 2H), 6.18 (s, 2H), 7.25–7.44 (m, 5H), 7.75–7.83 (m, 2H), 8.03 (d, J=8.2 Hz, 1H),

MS m/e 334 (MH$^+$).

| Anal. Calcd for C$_{20}$H$_{23}$N$_5$: | C, 72.04; H, 6.95; N, 21.00 |
|---|---|
| Found: | C, 71.73; H, 7.05; N, 21.06 |

EXAMPLE 23

1-[1-(3,5,5-Trimethyl-hexyl)-1H-benzimidazol-2-ylmethyl]-1H-benzotriazole

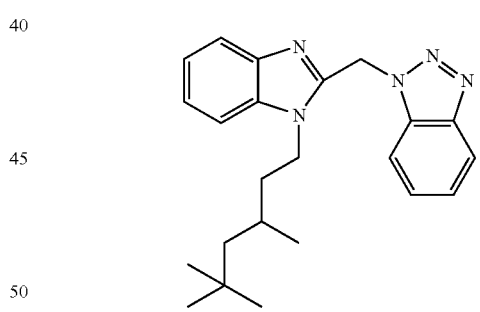

The general coupling procedure was applied using 1-bromo-3,5,5-trimethylhexane and sodium hydride in tetrahydrofuran to give the title compound in 41% yield:

IR (KBr, cm$^{-1}$): 2953, 1614, 1506, 1472, 1459, 750, 737.

$^1$H NMR (CDCl$_3$) δ 0.87 (s, 9H), 0.99 (d, J=6.6 Hz, 3H), 1.04–1.23 (m, 3H), 1.34–1.45 (m, 1H), 1.53–1.57 (m, 1H), 4.14–4.26 (m, 2H), 6.19 (s, 2H), 7.28–7.44 (m, 5H), 7.76–7.83 (m, 2H), 8.02 (bd, J=8.4 Hz, 1H).

MS m/e 376 (MH$^+$).

| Anal. Calcd for C$_{23}$H$_{29}$N$_5$.0.5H$_2$O: | C, 71.84; H, 7.86; N, 18.21 |
|---|---|
| Found: | C, 72.01; H, 7.82; N, 18.12 |

EXAMPLE 24

1-[1-(2-Methylthio-ethyl)-1H-benzimidazol-2-ylmethyl]-1H-benzotriazole

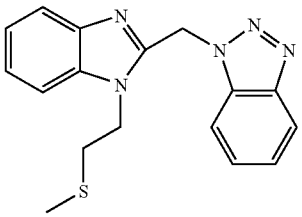

The general coupling procedure was applied using 2-chloroethylmethyl sulfide and sodium hydride in N,N-dimethylformamide to give the title compound in 44% yield:

IR (KBr, cm$^{-1}$): 1515, 1463, 1326, 1105, 738.

$^1$H NMR (CDCl$_3$) δ 2.05 (s, 3H), 2.63 (t, J=6.9 Hz, 2H), 4.50 (t, J=6.9 Hz, 2H), 6.31 (s, 2H), 7.29–7.37 (m, 4H), 7.44 (t, J=7.5 Hz, 1H), 7.81–7.84 (m, 2H), 8.03 (d, J=8.3 Hz, 1H).

MS m/e 324 (MH$^+$).

| Anal. Calcd for C$_{17}$H$_{17}$N$_5$S: | C, 63.13; H, 5.30; N, 21.65 |
|---|---|
| Found: | C, 63.05; H, 5.08; N, 21.59 |

EXAMPLE 25

1-[1-(2-Methylsulfinyl-ethyl)-1H-benzimidazol-2-ylmethyl]-1H-benzotriazole

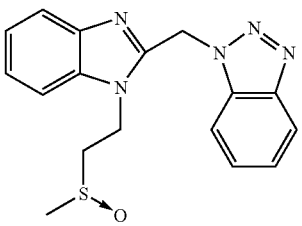

1-[1-(2-Methylthio-ethyl)-1H-benzimidazol-2-ylmethyl]-1H-benzotriazole (100 mg, 0.31 mmol) was dissolved in acetic acid (5 mL). Sodium perborate tetrahydrate (52 mg, 0.34 mmol) was added. The reaction mixture was stirred at 50° C. under nitrogen overnight. The acetic acid was evaporated under reduced pressure. Column chromatography (EtOAc, then EtOAc: MeOH=4:1) gave 84 mg (80%) of the title compound as a pale yellow solid.

IR (KBr, cm$^{-1}$): 3413, 1615, 1459, 1325, 1047, 743.

$^1$H NMR (CDCl$_3$) δ 2.53 (s, 3H), 2.53–2.79 (m, 2H), 4.68–7.47 (m, 1H), 4.90–5.00 (m, 1H), 6.20 (d, J=15.6 Hz, 1H), 6.37 (d, J=15.6 Hz, 1H), 7.28–7.39 (m, 3H), 7.43–7.53 (m, 2H), 7.78–7.82 (m, 1H), 7.85 (d, J=8.4 Hz, 1H), 8.02 (d, J=8.4 Hz, 1H).

MS m/e 340 (MH$^+$).

| Anal. Calcd for C$_{17}$H$_{17}$N$_5$OS.2H$_2$O: | C, 54.38; H, 5.64; N, 18.65. |
|---|---|
| Found: | C, 54.15; H, 4.61; N, 18.07. |

EXAMPLE 26

1-[1-(2-Methylsulfonyl-ethyl)-1H-benzimidazol-2-ylmethyl]-1H-benzotriazole

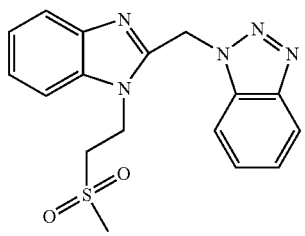

1-[1-(2-Methylthio-ethyl)-1H-benzimidazol-2-ylmethyl]-1H-benzotriazole (100 mg, 0.309 mmol) was dissolved in anhydrous N,N-dimethylformamide (5 mL). Magnesium monoperoxy phthalate hexahydrate (611 mg, 1.24 mmol) was added and the reaction mixture was stirred at room temperature overnight under N$_2$. The solvent was stripped under reduced pressure. The yellow oily residue was taken up in EtOAc (100 mL) and washed with water (2×50 mL) dried over magnesium sulfate, filtered and evaporated. Column chromatography on silica gel (EtOAc) gave 45 mg (41%) of the title compound as an oil.

IR (KBr): 2935, 1671, 1457, 1288, 1230, 1133, 754.

$^1$H NMR (CDCl$_3$) δ 2.95 (s, 3H), 3.09 (t, J=7.4 Hz, 2H), 4.87 (t, J=7.4 Hz, 2H), 6.26 (s, 2H), 7.30–7.40 (m, 4H), 7.50 (t, J=8.1 Hz, 1H), 7.80–7.83 (m, 1H), 7.84 (d, J=7.5 Hz, 1H), 8.04 (d, J=1H).

MS m/e 356 (MH$^+$).

EXAMPLE 27

1-(2-Benzotriazol-1-ylmethyl-1-H-benzimidazol-1-yl)-3,3-dimethylbutan-2-ol

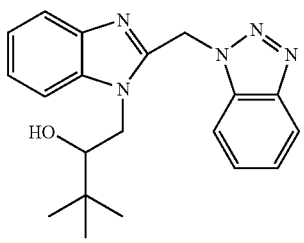

1-(2-Benzotriazol-1-ylmethyl-1-H-benzimidazol-1-yl)-3,3-dimethylbutan-2-one

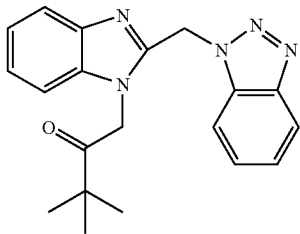

The general coupling procedure was applied using 1-bromopinacolone and sodium hydride in tetrahydrofuran to give the title compound in 61% yield:

IR (KBr, cm−1): 2969, 1722, 1463, 1085, 749.

$^1$H NMR (CDCl$_3$) δ 1.30 (s, 9H), 5.25 (s, 2H), 6.09 (s, 2H), 6.99–7.02 (m, 1H), 7.49–7.25 (m, 4H), 7.86–7.82 (m, 2H), 7.99 (d, J=7.5 Hz, 1H),

MS m/e 348 (MH$^+$).

| Anal. Calcd. for C$_{20}$H$_{21}$N$_5$O: | C, 69.14; H, 6.09; N, 20.16 |
|---|---|
| | C, 68.89; H, 6.20; N, 19.97. |

To a solution of 1-(2-benzotriazol-1-ylmethyl-1-H-benzoimidazol-1-yl)-3,3-dimethylbutan-2-one (75 mg, 0.216 mmol) in methanol (5 mL) was added sodium borohydride (100 mg, 2.64 mmol) at 0° C. The reaction mixture was stirred at 0° C. for two hours and at room temperature for two hours. The solvent was removed, the residue was diluted with water, extracted with methylene chloride. The combined extracts were dried over magnesium sulfate. Solvent was evaporated to give 42 mg of the product.

IR(KBr, cm−1): 3258, 2945, 2862, 1452, 1434, 1076, 743.

$^1$H NMR (CDCl$_3$) δ 1.12 (s, 9H), 2.35 (d, J=4.5 Hz, 1H), 3.59–3.64 (m, 1H), 4.41 (dd, J=10.4, 14.8 Hz, 1H), 4.25 (dd, J=2.0, 14.8 Hz, 1H), 5.96 (d, J=15.4 Hz, 1H), 6.58 (d, J=15.4 Hz, 2H), 7.21–7.46 (m, 5H), 7.70–7.73 (m, 1H), 7.82 (d, J=8.3 Hz, 1H), 8.00 (d, J=8.3 Hz, 1H).

MS m/e 350 (MH$^+$).

| Anal. Calcd. for C$_{20}$H$_{23}$N$_5$O.0.1H$_2$O: | C, 68.39; H, 6.66; N, 19.94 |
|---|---|
| Found: | C, 68.12; H, 6.72; N, 19.78. |

EXAMPLE 28

1-(2-[1,3]-Dioxolan-2-yl-methyl)-1H-benzimidazol-2-ylmethyl)-1H-benzotriazole

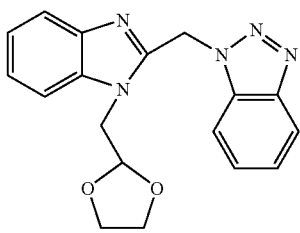

To a solution of 1-(1H-benzimidazol-2-ylmethyl)-1H-benzotriazole (1.0 g, 4.0 mmol) in anhydrous dimethyl sulfoxide (10 mL) was added potassium tert-butoxide (1.94 g, 4.0 mmol). The mixture was stirred at room temperature under nitrogen for 2 hours, followed by addition of a solution of potassium iodide (40 mg) and 2-bromomethyl-1,3-dioxolane (1.94 g, 11.6 mmol) in anhydrous dimethyl sulfoxide (5 mL). The reaction was stirred overnight, and the resulting mixture was poured into saturated aqueous ammonium chloride (10 mL) and extracted with ethyl acetate. The combined extracts were washed with saturated aqueous sodium bicarbonate (2×20 mL), brine, dried over sodium sulfate, and evaporated. The residue was purified by flash chromatography (EtOAc-Hexane=1:1) to give 152 mg (11%) of the title compound.

IR (KBr, cm−1): 2887, 1464, 1439, 1416, 1082, 757, 740.

$^1$H NMR (DMSO-d$_6$) δ 3.49–3.68 (m, 2H), 3.71–3.78 (m, 2H), 4.62 (d, J=3.2 Hz, 2H), 5.21 (t, J=3.2 Hz, 1H), 6.38 (s, 2H), 7.10–7.25 (m, 2H), 7.38–7.60 (m, 4H), 7.75–7.83 (m, 1H), 8.07 (d, J=8.3 Hz, 1H).

MS m/e 336 (MH$^+$).

| Anal. Calc for C$_{18}$H$_{17}$N$_5$O$_2$: | C, 64.47; H, 5.11; N, 20.88 |
|---|---|
| Found: | C, 64.17; H, 4.97; N, 21.27 |

EXAMPLE 29

1-(2-[1,3]-Dioxolan-2-yl-ethyl)-1H-benzimidazol-2-ylmethyl)-1H-benzotriazole

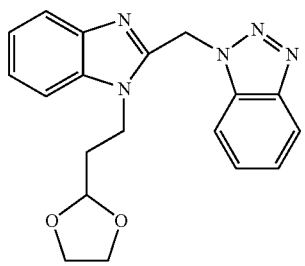

The general coupling procedure was applied using 2-(2-bromoethyl)-dioxalane and potassium carbonate in N,N-dimethylformamide to give the title compound in 59% yield:

IR(KBr, cm−1): 2883, 1614, 1512, 1409, 1131.

$^1$H NMR (CDCl$_3$) δ 1.92–1.98 (m, 2H), 3.83–3.88 (m, 2H), 3.97–4.01 (m, 2H), 4.46 (t, J=7.1 Hz, 2H), 4.83 (t, J=4.4 Hz, 1H), 6.25 (s, 2H), 7.25–7.47 (m, 5H), 7.80–7.85 (m, 2H), 8.02 (d, J=8.2 Hz, 1H).

MS m/e 350 (MH$^+$).

| Anal. Calcd for C$_{19}$H$_{19}$N$_5$O$_2$.0.1H$_2$O: | C, 64.98; H, 5.51; N, 19.94 |
|---|---|
| Found: | C, 64.75; H, 5.74; N, 19.76 |

EXAMPLE 30

1-[(2-Benzotriazol-1-ylmethyl)-1-H-benzimidazol-1-yl]-propionaldehyde

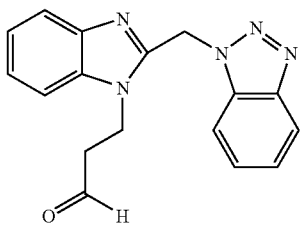

1-(2-[1,3]Dioxolan-2-yl-ethyl)-1H-benzimidazol-2-ylmethyl)-1H-benzotriazole (100 mg, 0.286 mmol) in 3 mL of 1 N HCl was stirred at room temperature for 2 days. The reaction solution was neutralized with sodium bicarbonate and extracted with methylene chloride. The combined extracts were dried over magnesium sulfate, and evaporated to give a white solid product.

IR (KBr, cm$^{-1}$): 3416, 2923, 1711, 1610, 1464, 1095.

$^1$H NMR (CDCl$_3$) δ 2.72 (t, J=6.5 Hz, 2H), 4.59 (t, J=6.5 Hz, 2H), 6.29 (s, 2H), 7.19–7.43 (m, 5H), 7.72–7.82 (m, 2H), 7.97 (d, J=8.1 Hz, 1H), 9.64 (s, 1H),

MS m/e 306 (MH$^+$).

EXAMPLE 31

2-(2-Benzoatrizol-1-ylmethyl-benzimidazol-1-yl)-ethanol

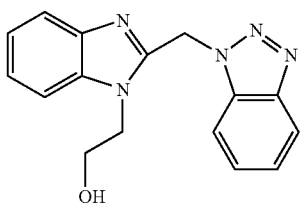

1-(1H-Benzimidazol-2-ylmethyl)-1H-benzotriazole (1 g, 4 mmol) and ethylene carbonate (10 g, 114 mmol) were stirred at 120° C. for 7 hours. The reaction mixture was cooled and diluted with water. The aqueous layer was extracted with methylene chloride (3×150 mL). The combined organic layers were dried over magnesium sulfate, filtered, and evaporated. The residue was purified by flash chromatography (EtOAc/hexane=12:1) to give 375 mg (32%) of the title compound as a white solid.

IR (KBr, cm$^{-1}$): 3233, 2922, 1731, 1613, 1432, 1068, 746.

$^1$H NMR (CDCl$_3$) δ 4.01–4.10 (m, 2H), 4.70–4.73 (m, 2H), 6.26 (s, 2H), 7.25–7.45 (m, 5H), 7.69 (d, J=7.6 Hz, 1H), 7.86 (d, J=8.4 Hz, 1H), 7.98 (d, J=8.4 Hz, 1 H

MS m/e 294 (MH$^+$).

EXAMPLE 32

Methanesulfonic Acid, 2-(2-benzotriazol-1-ylmethyl-benzimidazol-1-yl)-ethyl ester

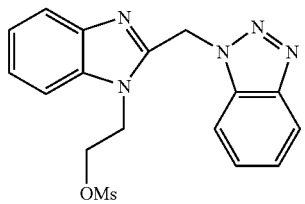

1-[1-(2-Hydroxylethyl)-1-H-benzimidazol-2-ylmethyl)-1H-benzotriazole (300 mg, 1.02 mmol) was suspended in anhydrous methylene chloride and cooled to 0° C. with an ice bath. Diisopropylethylamine (0.36 ml, 2.05 mmol) and methanesulfonyl chloride (0.16 mL, 2.05 mmol) were slowly added. The reaction was stirred at 0° C. for 1 hour during which the solution became clear. The solvent was stripped under vacuum, and the residue was purified by flash chromatography (EtOAc) to give 221 mg (58%) of the title compound as a white solid.

IR (KBr, cm$^{-1}$): 3015, 2935, 1617, 1514, 1460, 1339, 1162, 741.

$^1$H NMR (CDCl$_3$) δ 2.75 (s, 3H), 4.28 (t, J=5.5 Hz, 2H), 4.72 (t, J=5.5 Hz, 2H), 6.25 (s, 2H) 7.31–7.40 (m, 4H), 7.49 (bt, J=7.2 Hz, 1H), 7.81–7.84 (m, 1H), 7.88 (d, J=8.3 Hz, 1H), 8.04 (d, J=8.4 Hz, 1H).

MS m/e 372 (MH$^+$).

| Anal. Calcd for C$_{17}$H$_{17}$N$_5$O$_3$S: | C, 54.98; H, 4.61; N, 18.86 |
|---|---|
| Found: | C, 54.90; H, 4.64; N, 18.58 |

EXAMPLE 33

1-[1-(2-Azido-ethyl)-1-H-benzimidazol-2-ylmethyl)-1H-benzotriazole

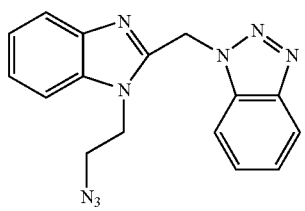

Sodium azide (350 mg, 5.38 mmol) was added to a solution of methanesulfonic acid, 2-(2-benzotriazol-1-ylmethyl-benzimidazol-1-yl)-ethyl ester (200 mg, 0.54 mmol) in 5 mL of anhydrous N,N-dimethylformamide. The reaction temperature was raised to 105° C. and stirred for 4 hours. The mixture was cooled, diluted with water and extracted with diethyl ether (3×100 mL). The combined ether extracts were dried over magnesium sulfate, filtered, and evaporated under vacuum. This gave the title compound as a white solid (160 mg, 94% yield).

IR (KBr, cm$^{-1}$): 2955, 2122, 2097, 1616, 1514, 1464, 1329, 741.
$^1$H NMR (CDCl$_3$) δ 3.50 (t, J=5.6 Hz, 2H), 4.40 (t, J=5.6 Hz, 2H), 6.21 (s, 2H), 7.25–7.42 (m, 5H), 7.75–7.80 (m, 2H), 7.97 (d, J=8.3, 1H).
MS m/e 319 (MH$^+$).

| Anal. Calcd for C$_{16}$H$_{14}$N$_8$: | C, 60.37; H, 4.43; N, 35.20 |
|---|---|
| Found: | C, 60.18; H, 4.48; N, 34.76 |

EXAMPLE 34

2-(2-Benzotriazol-1-ylmethyl-benzimidazol-1-yl)-ethyl-amine

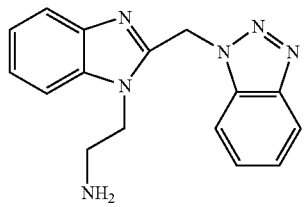

A mixture of 1-[1-(2-azido-ethyl)-1-H-benzimidazol-2-ylmethyl)-1H-benzotriazole (25 mg, 0.078 mmol) and 10% palladium on carbon in 1 mL of methanol was agitated under hydrogen at 55 psi for 5 hours. The reaction mixture was filtered through a pad of Celite and then through a Millipore membrane filter rinsing with methanol. The filtrate was stripped of solvent and dried under vacuum to give the amine (23 mg, quantitative yield) as a white solid.
$^1$H NMR (CD$_3$OD) δ 2.84 (t, d=6.8 Hz, 3H), 4.47 (t, J=6.8 Hz, 3H), 6.37 (s, 2H), 7.25–7.35 (m, 2H), 7.44 (t, d=8.3 Hz, 1H), 7.53–7.64 (m, 2H), 8.00 (d, J=7.7 Hz, 2H), 8.03 (d, J=8.2 Hz, 1H).
MS m/e 293 (MH$^+$).

EXAMPLE 35

2-(2-Benzotriazol-1-ylmethyl-benzimidazol-1-yl)-N-methyl acetamide

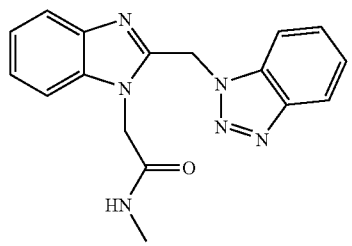

1-(1H-Benzimidazol-2-ylmethyl)-1H-benzotriazole (500 mg, 2.00 mmol) was dissolved in anhydrous N,N-dimethylformamide (10 mL). Potassium carbonate (1.11 g, 8.00 mmol) and 2-Chloro-N-methylacetamide (237 mg, 2.20 mmol) were added. The reaction mixture was allowed to stir overnight at reflux. The solvent was evaporated under vacuum, and the white waxy residue taken up in methylene chloride (300 mL). The organic extract was washed with saturated aqueous sodium bicarbonate (2×100 mL), dried over magnesium sulfate, filtered and evaporated. The residue was purified by chromatography (CH$_2$Cl$_2$/MeOH=15:1) to give 304 mg (47%) of the title compound as a white solid.
IR (KBr, cm$^{-1}$): 3315, 1660, 1580, 1466, 1265, 745.
$^1$H NMR (CDCl$_3$) δ 2.55 (d, J=4.8 Hz, 3H), 4.93 (s, 2H), 5.42 (bs, 1H), 6.18 (s, 2H), 7.27–7.39 (m, 4H), 7.49 (dt, J=0.9, 8.2 Hz, 1H), 7.79–7.83 (m, 2H), 8.04 (d, J=8.4 Hz, 1H).
MS m/e 320 (MH$^+$).

| Anal. Calcd for C$_{17}$H$_{16}$N$_6$O·0.1H$_2$O: | C, 63.38; H, 5.07; N, 26.09 |
|---|---|
| Found: | C, 63.09; H, 4.88; N, 26.19 |

EXAMPLE 36

[2-(2-Benzotriazol-1-ylmethyl-benzimidazol-1-yl)-ethyl]-methyl-amine

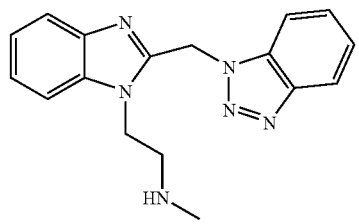

In an oven dried round bottom flask, lithium aluminum hydride (26 mg, 0.69 mmol) and aluminum chloride (97 mg, 0.73 mmol) were stirred in 10 mL of anhydrous tetrahydrofuran at 70–80° C. for 1 hour. 2-(2-Benzotriazol-1-ylmethyl-1-H-benzimidazol-1-yl)-N-methyl acetamide (50 mg, 0.156 mmol) was added. After 3 hours, more lithium aluminum hydride (1 M in tetrahydrofuran, 0.312 mL, 0.312 mmol) was added. The reaction mixture was allowed to stirred for 2 additional hours. The solvent was evaporated, and the residue was purified by flash chromatography (CH$_2$Cl$_2$/MeOH=15:1) to give 14 mg (28%) of the title compound as an oil.
$^1$H NMR (CDCl$_3$) δ 2.40 (s, 3H), 2.73 (t, J=6.3 Hz, 2H), 4.41 (t, J=6.3 Hz, 2H), 6.29 (s, 2H), 7.25–7.46 (m, 5H), 7.81 (bd, J=8.4 Hz, 1H), 8.01 (bd, J=8.3 Hz, 1H).
MS m/e 307 (MH$^+$).

EXAMPLE 37

4-(2-Benzotriazol-1-ylmethyl)-benzimidazol-1-yl)-butan-2-one

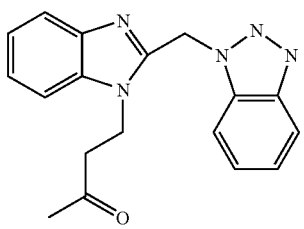

1-(1H-Benzimidazol-2-ylmethyl)-1H-benzotriazole (0.20 g, 0.80 mmol) was suspended in acetonitrile (10 mL). Methyl vinyl ketone (67 mg, 0.962 mmol) was added followed by 1,3,4,6,7,8-hexahydro-1-methyl-2H-pyrimido[1,2-a] pyrimidine (MTBD, 6 mg, 0.040 mmol). The reaction mixture was heated at 80° C. overnight under nitrogen. The solvent was stripped under reduced pressure. The residue was taken up in ether and washed with water (2×25 mL). The ether was dried over magnesium sulfate, filtered and evaporated. Column chromatography ($CH_2Cl_2$: MeOH=20:1) gave 44 mg (18%) of the title compound as a pale yellow solid.

IR (KBr, $cm^{-1}$): 1706, 1615, 1469, 1152, 744.

$^1$H NMR ($CDCl_3$) δ 2.07 (s, 3H), 2.66 (t, J=6.5 Hz, 2H), 4.57 (t, J=6.5 Hz, 2H), 6.36 (s, 2H), 7.26–7.32 (m, 3H), 7.35 (d, J=1.0, 7.1 Hz, 1H), 7.46 (dt, J=0.9, 7.0 Hz, 1H), 7.78–7.81 (m, 1H), 7.85 (d, J=8.3 Hz, 1H), 8.03 (d, J=8.3 Hz, 1H).

MS m/e 320 (MH$^+$).

| Anal. Calcd for $C_{18}H_{17}N_5O \cdot 0.5H_2O$: | C, 65.84, H, 5.53; N, 21.33. |
|---|---|
| Found: | C, 66.00; H, 5.28; N, 20.95. |

EXAMPLE 38

4-(2-Benzotriazol-1-ylmethyl)-benzimidazol-1-yl)-butan-2-ol

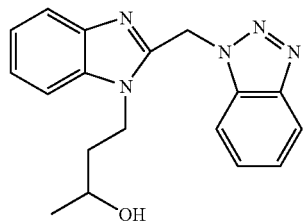

1-(1H-Benzimidazol-2-ylmethyl)-1H-benzotriazole (0.30 g, 1.2 mmol), methyl vinyl ketone (126 mg, 1.8 mmol) and Triton B (40% in methanol, two drops) in pyridine (5 mL) were stirred at reflux overnight. The solvent was evaporated and the residue was dissolved in 5 mL of alcohol and sodium borohydride (91 mg, 2.4 mmol) was added. After stirring at room temperature for 2 hours, the reaction mixture was adjusted to pH 5 with concentrated HCl. The solvent was evaporated. The residue was diluted with water and extracted with ethyl acetate. The combined extracts were dried over magnesium sulfate and evaporated. The residue was purified by flash chromatography (EtOAc:hexane=2:1 to straight EtOAc) to give a product which was triturated in hexane-ether to provide 81 mg (21%) of the product as a pale solid.

IR (KBr, cm–1): 3369, 2959, 1458, 1426, 1103, 736.

$^1$H NMR ($CDCl_3$) δ 1.14 (d, J=6.2 Hz, 1H), 1.40–1.59 (m, 2H), 1.75 (d, J=5.6 Hz, 1H), 3.69–3.73 (m, 1H), 4.07–4.55 (m, 2H), 6.19 (d, J=15.5 Hz, 1H), 6.36 (d, J=15.5 Hz, 1H), 7.26–7.37 (m, 4H), 7.44 (t, J=8.0 Hz, 1H), 7.77–7.84 (m, 2H), 8.02 (d, J=8.3 Hz, 1H).

MS m/e 322 (MH$^+$).

| Anal. Calcd for $C_{18}H_{19}N_5O$: | C, 67.27, H, 5.96; N, 21.79 |
|---|---|
| Found: | C, 67.03; H, 6.15; N, 21.24 |

EXAMPLE 39

4-(2-Benzotriazol-1-ylmethyl)-benzimidazol-1-yl)-butan-2-one, Oxime

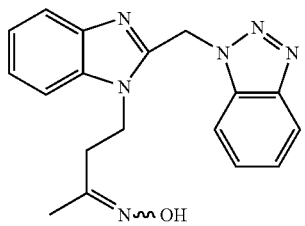

To a suspension of 4-(2-benzotriazol-1-ylmethyl)-benzimidazol-1-yl)-butan-2-one (24 mg, 0.075 mmol) in absolute ethanol (10 mL) was added triethylamine (8 mg, 0.075 mmol) followed by hydroxylamine hydrochloride (7.3 mg, 0.105 mmol). The mixture was refluxed overnight under nitrogen. The solvent was removed under reduced pressure. The resulting residue was diluted with saturated aqueous sodium bicarbonate and extracted with methylene chloride. The combined extracts were dried over magnesium sulfate, filtered and evaporated to give 25 mg (quantitative yield) of the title compound as a mixture of E and Z isomers.

IR (KBr, $cm^{-1}$): 3064, 1473, 1422, 1083, 744.

$^1$H NMR ($CDCl_3$) δ 1.65 and 1.79 (s, 3H), 2.50–2.60 (m 2H), 4.54–4.59 (m,2H), 6.39 (s, 2H), 7.15–7.45 (m, 3H), 7.52–7.57 (m, 3H), 7.80–7.87 (m, 1H), 8.07–8.10 (m, 1H).

MS m/e 335 (MH$^+$).

EXAMPLE 40

3-(2-Benzotriazol-1-ylmethyl-benzimidazol-1-yl)-1-methyl-propylamine

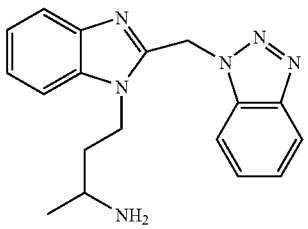

To a solution of lithium aluminum hydride (8.4 mg, 0.318 mmol) in tetrahydrofuran (5 mL) at 0° C., 4-(2-benzotriazol-1-ylmethyl)-benzimidazol-1-yl)-butan-2-one, oxime (24 mg, 0.071 mmol) in tetrahydrofuran (5 mL) was slowly added over 5 minutes. The reaction mixture was refluxed overnight. The reaction was quenched with 10 N NaOH (0.70 mL). The mixture was stirred over the weekend. The solution was decanted, and the solvent was stripped. Column chromatography (EtOAc:MeOH=5:1 to 1:2) gave 8 mg (35% yield) of the product as a brown solid.

IR (KBr, cm$^{-1}$): 3435, 2933, 1575, 1423, 745.

$^1$H NMR (CDCl$_3$) δ 1.27 (d, J=7.5 Hz, 3H), 1.55–1.75 (m, 3H), 3.30–3.37 (m, 1H), 4.46–4.56 (m, 2H), 6.23 (d, J=15.9 Hz, 1H), 6.30 (d, J=15.9 Hz, 1H), 7.24–7.54 (m, 5H), 7.76–7.79 (m, 1H), 7.82 (d, J=7.8 Hz, 1H), 7.96 (d, J=8.1 Hz, 1H).

MS m/e 321 (MH$^+$).

EXAMPLE 41

3-(2-Benzotriazol-1-ylmethyl-1-H-benzimidazol-1-yl)-propionamide

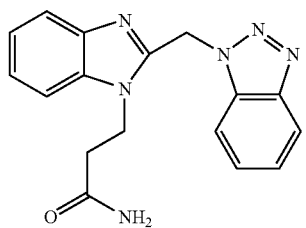

1-(1H-Benzimidazol-2-ylmethyl)-1H-benzotriazole (300 mg, 1.20 mmol) and acrylamide (86 mg, 1.20 mmol) were dissolved in pyridine (5 mL). Triton B (40% by weight in methanol, 0.010 mL, 0.024 mmol) was added at room temperature. The temperature was slowly raised to reflux. The reaction mixture was stirred at reflux overnight under nitrogen. The solvent was stripped under reduced pressure. The residue was taken up in aqueous saturated sodium bicarbonate solution and extracted with EtOAc (4×100 mL). The combined organic extracts were dried over magnesium sulfate, filtered and evaporated. The residue was purified by chromatography (EtOAc/MeOH 12:1 to 4:1) to give 128 mg (33%) of the title compound as a white solid.

IR (KBr, cm$^{-1}$): 3778, 1675, 1467, 1455, 743.

$^1$H NMR (DMSO-d$_6$) δ 2.67 (t, J=6.4 Hz, 2H), 4.59 (t, J=6.4 Hz, 2H), 6.48 (s, 2H), 7.02 (bs, 1H), 7.16 (t, J=7.3 Hz, 1H), 7.25 (t, J=7.3 Hz, 1H), 7.39–7.61 (m, 4H), 7.82 (d, J=8.3 Hz, 1H), 8.08 (d, J=8.3 Hz, 1H).

MS m/e 321 (MH$^+$).

EXAMPLE 42 t-Butyl 3-(2-benzotriazol-1-ylmethyl)-benzimidazol-1-yl)-propionate

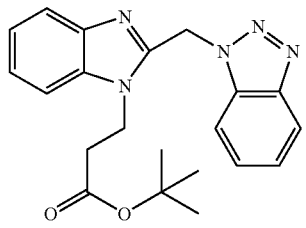

1-(1H-Benzimidazol-2-ylmethyl)-1H-benzotriazole (0.30 g, 1.2 mmol), t-butyl acrylate (185 mg, 1.44 mmol) and Triton-B (40% in MeOH, two drops) in anhydrous pyridine (5 mL) were stirred at reflux over night. The solvent was evaporated, the residue was diluted with water, and extracted with diethyl ether. The combined extracts were dried over magnesium sulfate and evaporated. The residue was purified by flash chromatography (EtOAc: hexane=1:2 ) to give 348 mg (77%) of the product as a solid.

IR (KBr, cm$^{-1}$): 1726, 1390, 1151, 736.

$^1$H NMR (CDCl$_3$) δ 1.36 (s, 9H), 2.60 (t, J=6.5 Hz, 2H), 4.58 (t, J=6.5 Hz, 2H), 6.38 (s, 2H), 7.27–7.35 (m, 4H), 7.45 (t, J=7.0 Hz, 1H), 7.78–7.81 (m, 1H), 7.88 (d, J=8.3 Hz, 1H), 8.02 (d, J=8.3 Hz, 1H).

MS m/e 378 (MH$^+$).

| Anal. Calcd for C$_{21}$H$_{23}$N$_5$O$_2$: | C, 66.83; H, 6.14; N, 18.55. |
|---|---|
| Found: | C, 66.99; H, 6.17; N, 18.53. |

EXAMPLE 43

3-(2-Benzotriazol-1-ylmethyl)-benzimidazol-1-yl)-propionic acid

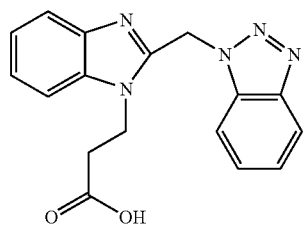

t-Butyl 3-(2-benzotriazol-1-ylmethyl)-benzimidazol-1-yl)-propionate (100 mg, 0.27 mmol) was stirred in 50% trifluoroacetic acid in methylene chloride (3 mL) overnight. The solvent was evaporated, and the residue was diluted with saturated sodium bicarbonate solution, and 1 N HCl to pH 6. The solution was extracted with ethyl acetate. The combined extracts were dried over magnesium sulfate and evaporated. The residue was triturated in a mixture of ethyl acetate and diethyl ether to give 71 mg (83%) of the product as a pale solid.

IR (KBr, cm$^{-1}$): 3420, 1705, 1441, 1269, 1212, 744.

$^1$H NMR (DMSO-d$_6$) δ 2.77 (t, J=6.9 Hz, 2H), 4.60 (t, J=6.9 Hz, 2H), 6.46 (s, 2H), 7.15–7.28 (m, 2H), 7.43 (t, J=7.0 Hz, 1H), 7.52–7.57 (m, 2H), 7.63 (d, J=8.0 Hz, 1H), 7.83 (d, J=8.3 Hz, 1H), 8.09 (d, J=8.3 Hz, 1H).

MS m/e 322 (MH$^+$).

| Anal. Calcd for C$_{17}$H$_{15}$N$_5$O$_2$: | C, 63.54; H, 4.70; N, 21.79. |
|---|---|
| Found: | C, 63.35; H, 4.88; N, 21.84. |

EXAMPLE 44

N-[3-(2-Benzotriazol-1-ylmethyl-benzimidazol-1-yl)-1-imino-propyl]-hydroxyamine

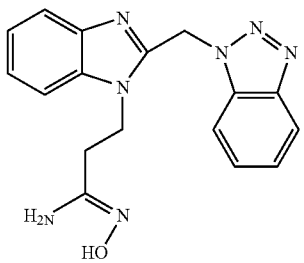

3-(2-Benzotriazol-1-ylmethyl-1-H-benzimidazol-1-yl)-propionitrile

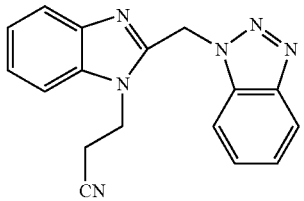

To 1-(1H-benzimidazol-2-ylmethyl)-1H-benzotriazole (100 mg, 0.40 mmol) suspended in 5 mL of acetonitrile under nitrogen atmosphere was added acrylonitrile (0.032 mL, 0.48 mmol), followed by 1,3,4,6,7,8-hexahydro-1-methyl-2H-pyrimido[1,2-a] pyrimidine (MTBD, 0.003 mL, 0.020 mmol). The reaction mixture was heated to 80° C. for 6 hours. The solvent was stripped. The residue was taken up in ether and washed with water. Column chromatography (EtOAc/hexane=10:1) of the residue gave 45 mg (37%) of the product as a pale yellow solid.

IR (KBr, cm–1): 3057, 2921, 2255, 1616, 1461, 1329, 739.

$^1$H NMR (CDCl$_3$) δ 2.65 (t, J=6.6 Hz, 2H), 4.70 (t, J=6.6 Hz, 2H), 6.25 (s, 2H), 7.30–7.40 (m, 4H), 7.47–7.52 (m, 1H), 7.81–7.87 (m, 2H), 8.04 (d, J=8.4 Hz, 1H).

MS m/e 303 (MH$^+$).

| Anal. Calcd for C$_{17}$H$_{14}$N$_6$·0.25H$_2$O: | C, 66.54; H, 4.76; N, 27.39 |
|---|---|
| Found: | C, 66.53; H, 4.60; N, 27.19 |

3-(2-Benzotriazol-1-ylmethyl-1-H-benzimidazol-1-yl)-propionitrile (100 mg, 0.33 mmol), hydroxylamine hydrochloride (83 mg, 1.19 mmol) and potassium carbonate (87 mg, 0.63 mmol) were dissolved in a mixture of ethanol and water (2:1, 7.5 mL). The solution was stirred at room temperature for 10 minutes and then at reflux overnight. The solvent was evaporated, and the residue diluted with water and extracted with methylene chloride (3×50 mL). The combined organic fractions were dried over magnesium sulfate, and evaporated. Column chromatography (EtOAc to EtOAc:MeOH=10:1, gradient) gave 71 mg (64% yield) the title compound as a pale yellow solid.

IR (KBr, cm–1): 3110, 1670, 1473, 1422, 747.

$^1$H NMR (CDCl$_3$) δ 2.18 (t, J=7.5 Hz, 2H), 4.60 (t, J=7.5 Hz, 2H), 4.79 (bs, 2H), 6.23 (s, 2H), 7.25–7.47 (m, 5H), 7.80–7.82 (m, 1H), 7.84 (d, J=7.5 Hz, 1H), 8.02 (d, J=8.4 Hz, 1H).

MS m/e 336 (MH$^+$).

EXAMPLE 45

3-(2-Benzotriazol-1-ylmethyl-benzimidazol-1-yl)-1-imino-1propyl-amine Diacetate

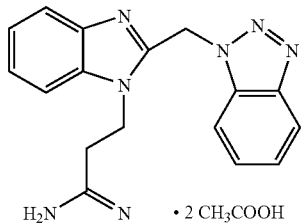

N-[3-(2-Benzotriazol-1-ylmethyl-benzimidazol-1-yl)-1-imino-propyl]-hydroxyamine (57 mg, 0.17 mmol) was dissolved in acetic acid (1 mL). Acetic anhydride was added and the solution was stirred at room temperature for 5–10 minutes. The solution was then added to 10% Pd/C (15 mg) in a Parr reaction vessel. The mixture was agitated under H$_2$ (at 55 psi) for 4 hours. The catalyst was removed by filtration. Evaporation of the filtrate gave a yellow gum which was azeotroped with hexane several times. Trituration with diethyl ether gave 64 mg (64% yield) of the title compound as a tan solid.

IR (KBr, cm–1): 3027, 1685, 1513, 1281, 746.

$^1$H NMR (DMSO-d$_6$) δ 1.81 (s, 6H), 2.94 (t, J=7.4 Hz, 2H), 4.75 (t, J=7.4 Hz, 2H), 6.46 (s, 2H), 7.20 (t, J=7.3 Hz, 1H), 7.30 (t, J=7.2 Hz, 1H), 7.45 (t, J=8.1 Hz, 1H), 7.51–7.61 (m, 2H), 7.74 (d, J=8.0 Hz, 1H), 7.88 (d, J=8.3 Hz, 1H), 8.11 (d, J=8.4 Hz, 1H).

MS m/e 320 (MH$^+$).

EXAMPLE 46

1-[(1-Phenylmethyl-1H-benzimidazol)-2-ylmethyl]-1H-benzotriazole

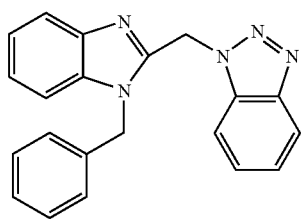

The general coupling procedure was applied using benzyl bromide and sodium hydride in tetrahydrofuran to give the title compound in 95% yield:

IR (KBr, cm$^{-1}$): 1494. 1436, 1323, 1227, 753, 729.

$^1$H NMR (CDCl$_3$) d 5.48 (s, 2H), 6.14 (s, 2H), 6.84 (dd, d=8.0 Hz, 1H), 6.83–7.45 (m, 9H), 7.79 (d, J=8.2 Hz, 1H), 7.86 (d, J=7.1 Hz, 1H), 7.94 (d, J=8.1 Hz, 1H).

MS m/e 340 (MH$^+$).

| | |
|---|---|
| Anal. Calcd for C$_{21}$H$_{17}$N$_5$·0.25H$_2$O: | C, 73.34; H, 5.13; N, 20.36 |
| Found: | C, 73.62; H, 5.22; N, 20.28 |

EXAMPLE 47

1-[1-(Pyridin-3-yl-methyl)-1H-benzimidazol-2-ylmethyl]-1H-benzotriazole

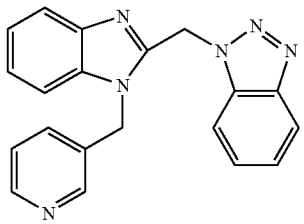

The general coupling procedure was applied using 3-picolyl chloride hydrochloride and sodium hydride in tetrahydrofuran to give the title compound in 31% yield:

IR(KBr, cm$^{-1}$): 3423, 1578, 1452, 1425, 1335, 1240, 1089, 749.

$^1$H NMR (CDCl$_3$) δ 5.53 (s, 2H), 6.17 (s, 2H), 6.97–6.99 (m 1H), 7.44 (t, J=7.0 Hz, 1H), 7.17–7.37 (m, 7H), 7.76 (d, J=8.3 Hz, 1H), 7.88 (d, J=8.0 Hz, 1H), 7.93 (d, J=7.5 Hz, 1H).

MS m/e 341 (MH$^+$).

EXAMPLE 48

1-[1-(2-Phenethyl)-1-H-benzimidazol-2-ylmethyl)-1H-benzotriazole

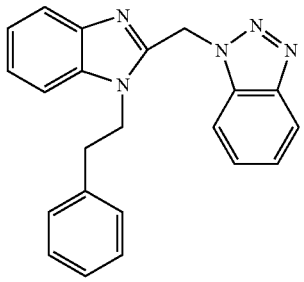

1-(1H-Benzimidazol-2-ylmethyl)-1H-benzotriazole (374 mg, 1.5 mmol), phenethyl alcohol (0.12 mL, 1.0 mmol), and tributylphosphine (0.37 mL, 1.5 mmol) were mixed in 10 mL of anhydrous benzene under nitrogen. The mixture was cooled in an ice bath, and 1,1'-(azodicarbonyl)-dipiperidine (378 mg, 1.5 mmol) was added. After stirring for 15 minutes at 0° C., the reaction was allowed to warm to room temperature and stirred overnight. The solvent was evaporated and column chromatography of the residue (EtOAc/hexane=1:1 to EtOAc/hexane=3:1, gradient) gave the title compound as a pale yellow solid (63 mg, 18% yield).

IR (KBr, cm$^{-1}$): 1615, 1495, 1471, 1454, 1075, 744.

$^1$H NMR (CDCl$_3$) δ 2.76 (t, J=7.1 Hz, 2H), 4.42 (t, J=7.1 Hz, 2H), 5.54 (s,2H), 6.95 (bd, J=7.8 Hz, 2H), 7.19–7.37 (m, 8H), 7.68 (d, J=8.4 Hz, 1H), 7.75–7.78 (m, 1H), 7.95 (d, J=7.9 Hz, 1H).

MS m/e 354 (MH$^+$).

| | |
|---|---|
| Anal. Calcd for C$_{22}$H$_{19}$N$_5$·0.25H$_2$O: | C, 73.83; H, 5.49; N, 19.57 |
| Found: | C, 73.72; H, 5.48; N, 19.24 |

EXAMPLE 49

2-[(2-Benzotriazol-1-ylmethyl)-benzimidazol-1-yl]-1-phenyl-ethanone

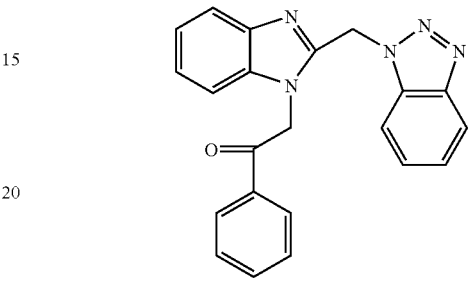

The general coupling procedure was applied using 2-bromoacetophenone and sodium hydride in N,N-dimethylformamide to give the title compound in 27% yield:

IR (KBr, cm$^{-1}$): 1697, 1466, 1449, 747.

$^1$H NMR (DMSO-d$_6$) δ 2.71 (s, CH$_3$, DMF), 2.87 (s, CH$_3$, DMF), 6.22 (s, 2H), 6.29 (s, 2H), 7.14–7.22 (m, 2H), 7.34–7.39 (m, 1H), 7.48–7.53 (m, 4H), 7.56–7.65 (m, 2H), 7.99 (s, HCO, DMF), 8.02–8.05 (m, 4H).

MS m/e 368 (MH$^+$).

| | |
|---|---|
| Anal Calc for C$_{22}$H$_{17}$N$_5$O·1.7H$_2$O·2.1DMF: | C, 61.63; H, 6.41; N, 18.03 |
| Found: | C, 61.48; H, 6.13; N, 17.87 |

EXAMPLE 50

2-[(2-Benzotriazol-1-ylmethyl)-benzimidazol-1-yl]-1-phenyl-ethanol

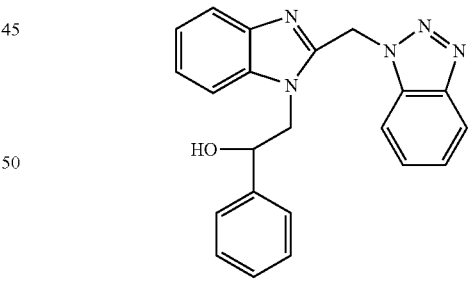

To a solution of 2-[(2-benzotriazol-1-ylmethyl)-benzimidazol-1-yl]-1-phenyl-ethanone (120 mg, 0.33 mmol) in methanol (5 mL) was added sodium borohydride (124 mg, 3.26 mmol) at 0° C. The reaction mixture was stirred at 0° C. for 2 hours and then at room temperature for additional 2 hours. Methanol was removed and the residue was diluted with water and extracted with methylene chloride. The combined organic extracts were dried over sodium sulfate and evaporated to give 71 mg (59% yield) of the title compound as a white solid.

IR(KBr, cm-1): 3209, 1453, 1430, 744, 699.

$^1$H NMR (DMSO-d$_6$) δ 4.41–4.53 (m, 2H), 4.87–4.91 (m, 1H), 5.91 (d, J=4.2 Hz, 1H), 6.25 (d, J=16.5 Hz, 1H), 6.37

(d, J=16.5 Hz, 1H), 7.11–7.28 (m, 2H), 7.31–7.42 (m, 4H), 7.47–7.60 (m, 5H) 7.75 (d, J=8.3 Hz, 1H), 8.06 (d, J=8.3 Hz, 1H).

MS m/e 370 (MH$^+$).

| Anal. Calc for C$_{22}$H$_{19}$N$_5$O.0.25EtOAc.0.1H$_2$O: | C, 66.30; H, 5.76; N, 16.81 |
|---|---|
| Found: | C, 66.19; H, 5.38; N, 17.06 |

EXAMPLE 57

[2-(2-Benzotriazol-2-ylmethyl)-benzimidazol-1-yl]-ethyl]-diisopropyl-amine Dihydrochloride

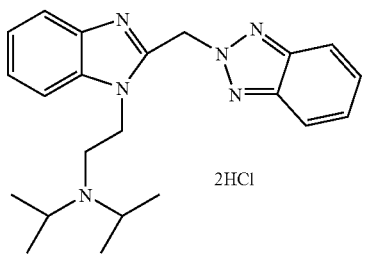

The general coupling procedure was applied using 2-(1H-benzimidazol-2-ylmethyl)-2H-benzotriazole, 2-diisopropylaminoethyl chloride hydrochloride and sodium hydride in N,N-dimethylformamide to give the title compound in 15% yield:

IR (KBr, cm$^{-1}$) 3400, 2973, 2654, 1461, 1328, 1140, 750.

$^1$H NMR (CD$_3$OD) δ 1.46 (d, J=6.4 Hz, 6H), 1.52 (d, J=6.4 Hz, 6H), 3.66–3.69 (m, 2H), 3.91–4.00 (m, 2H), 5.26–5.32 (m, 2H), 6.67 (s, 2H), 7.47–7.50 (m, 2H), 7.64–7.70 (m, 2H), 7.88–7.91 (m, 2H), 8.05 (d, J=8.4 Hz, 1H).

MS m/e 377 (MH$^+$).

| Anal. Calcd for C$_{22}$H$_{28}$N$_6$.2HCl.1.25H$_2$O: | C, 55.99; H, 6.94; N, 17.81 |
|---|---|
| Found: | C, 56.01; H, 6.74; N, 17.46 |

EXAMPLE 58

2-(2-Pyrrolidin-1-yl-ethyl)-1H-benzimidazol-2-ylm-ethyl)-2H-benzotriazole Dihydrochloride

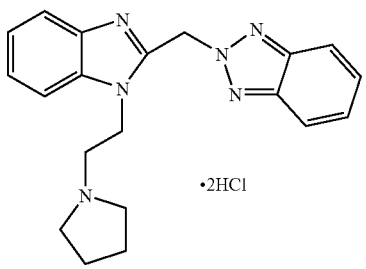

The general coupling procedure was applied using 2-(1H-benzimidazol-2-ylmethyl)-2H-benzotriazole, 1-(2–Chloroethyl)-pyrrolidine hydrochloride and sodium hydride in toluene to give the title compound in 38% yield:

IR(KBr, cm$^{-1}$): 3390, 2962, 2474, 1529, 1462, 1267.

$^1$H NMR (CD$_3$OD) δ 2.05–2.15 (m, 4H), 3.56–3.85 (m, 6H), 5.21–5.26 (m, 2H), 6.75 (s, 2 ), 7.48–7.52 (m, 2H), 7.64–7.75 (m, 2H), 7.84 (d, J=7.7 Hz, 1H), 7.90–7.94 (m, 2H) 8.105 (d, J=8.1 Hz, 1H),

MS m/e 347 (MH$^+$).

EXAMPLE 59

2-(2-Piperidin-1-yl-ethyl)-1H-benzimidazol-2-ylm-ethyl)-2H-benzotriazole Dihydrochloride

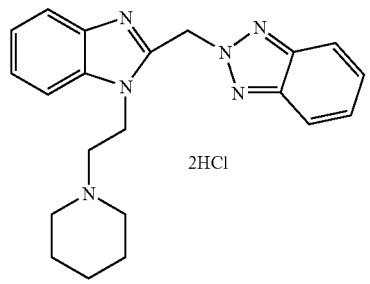

The general coupling procedure was applied using 2-(1H-benzimidazol-2-ylmethyl)-2H-benzotriazole, 1-(2-Chloroethyl)-piperidine hydrochloride and sodium hydride in toluene to give the title compound in 65% yield:

IR(KBr, cm$^{-1}$): 3435, 2916, 2721, 1728, 1615, 1452, 1417, 1276, 758.

$^1$H NMR (CD$_3$OD) δ 1.90–2.10 (m, 6H), 3.10–3.20 (m, 2H), 3.56–3.76 (m, 4H), 5.21–5.34 (m, 2H), 6.76 (s, 1H), 7.48–7.53 (m, 2H), 7.60–7.75 (m, 2H), 7.83 (d, J=7.7 Hz, 1H), 7.90–7.94 (m, 2H), 8.16 (d, J=8.1 Hz, 1H).

MS m/e 361 (MH$^+$).

EXAMPLE 60

2-(2-Azepin-1-yl-ethyl)-1H-benzimidazol-2-ylm-ethyl)-2H-benzotriazole Dihydrochloride

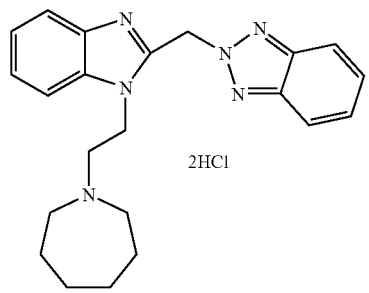

The general coupling procedure was applied using 2-(1H-benzimidazol-2-ylmethyl)-2H-benzotriazole and 2-(hexamethyleneimino)ethyl chloride hydrochloride and sodium hydride in tetrahydrofuran to give the title compound in 39% yield:

IR(KBr, cm$^{-1}$): 3430, 2926, 1617, 1526, 1456, 744.

¹H NMR (CD₃OD) δ 1.75–1.80 (m, 4H), 1.85–2.10 (m, 4H), 3.32–3.42 (m, 2H), 3.67–3.72 (m, 4H), 5.22–5.27 (m, 2H), 6.71 (s, 2H), 7.49–7.52 (m, 2H), 7.63–7.72 (m, 2H), 7.83 (d, J=7.6 Hz, 7.90–7.95 (m, 2H). 8.07 (d, J=7.9 Hz, 1H).

MS m/e 375 (MH⁺).

EXAMPLE 61

2-[1-(3-methylbutyl)-1H-benzimidazol-2-ylmethyl]-2H-benzotriazole Dihydrochloride

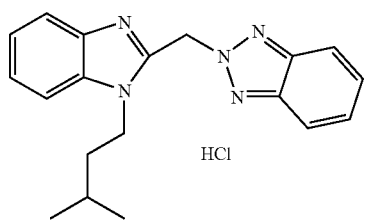

The general coupling procedure was applied using 2-(1H-benzimidazol-2-ylmethyl)-2H-benzotriazole, 1-bromo-3-methylbutane and sodium hydride in N,N-dimethylformamide to give the title compound in 30% yield:

IR (KBr, cm⁻¹): 2959.8, 1623.0, 1538, 1326.3, 754.

¹H NMR (DMSO-d₆) δ 0.91 (d, J=6.6 Hz, 6H), 1.37–1.45 (m, 2H); 1.65–1.75 (m, 1H), 4.62–4.68 (m, 2H), 6.67 (s, 2H), 7.48–7.56 (m, 2H), 7.69–7.74 (m, 2H), 7.86–7.94 (m, 4H).

MS m/e 320 (MH⁺).

| | |
|---|---|
| Anal. Calcd for C₁₉H₂₁N₅·HCl·¾H₂O: | C, 61.78; H, 6.65; N, 18.96; Cl, 9.60. |
| Found: | C, 61.87; H, 6.50; N, 18.98; Cl, 9.65. |

Biological Activity

The antiviral activity of these compounds against respiratory syncytial virus was determined in HEp-2 (ATCC CCL 23) cells that were seeded in 96 well microtiter plates at 1.5×10⁴cells/100 µL/well in DMEM (Dulbecco's Modified Eagle's Medium) supplemented with penicillin, streptomycin, glutamine, and 10% fetal bovine serum. The cells were incubated overnight at 37° C., the culture medium was removed, and cells were infected (100 µL volume in medium containing 2% fetal bovine serum) with respiratory syncytial virus Long strain at 5000 plaque forming units/mL. The compounds, 100 µL at appropriate dilution, were added to the cells 1 hour post infection. After incubation for 4 days at 37° C., the plates were stained with MTT solution (3-[4,5-dimethlythiazol-2-yl]-2,5-diphenyltetrazolium bromide) and incubated for 4 hours at 37° C. The media was aspirated from the cells and 100 µL/well of acidified isopropanol (per liter: 900 ml isopropanol, 100 ml Triton X100, and 4 ml conc. HCl) was added. Plates were incubated for 15 minutes at room temperature with shaking, and an optical density (OD 540) reading at 540 nanometer (nm) was obtained. The optical density reading is proportional to the number of viable cells. The increase in the number of viable cells reflects the protective, antiviral activity of the compound. Assays comparing MTT staining in uninfected cells containing compound with uninfected cells in the absence of compound provide a measure of cellular toxicity. The control compound in this assay is Ribavirin which exhibits 100% cell protection at 2.5 µg/mL (corresponding to 10.2 µM).

The antiviral activity of compounds is presented as a percentage of cell protection at a concentration of 4 µg/mL of the compound. The higher percentage of cell protection, the more potent is the compound. The CC₅₀ values, expressed in micromolars (µM), represent the concentration of the compound that results in a normalized OD540 reading half that of uninfected cells not treated with compound. The lower the concentration, the more cytotoxic is the compound. The CC₅₀ for Ribavirin in this assay is 9.5 µg/mL (corresponding to 40 µM). The data are shown in Table 1 and 2.

TABLE 1

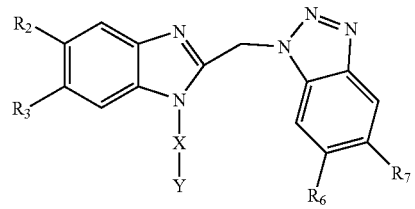

| Example No. | R₂ | R₃ | R₆ and R₇ | X—Y | % Cell protection at 4 µg/mL | CC₅₀ (µM) |
|---|---|---|---|---|---|---|
| 1 | H | H | H | ⁀NMe₂ | 100 | >100 |
| 2 | H | H | H | ⁀⁀NMe₂ | 100 | 197 |
| 3 | H | H | H | ⁀⁀NEt₂ | 100 | 215 |

TABLE 1-continued
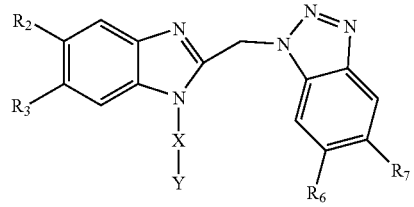
| Example No. | R₂ | R₃ | R₆ and R₇ | X—Y | % Cell protection at 4 μg/mL | CC₅₀ (μM) |
|---|---|---|---|---|---|---|
| 4 | H | H | H | (ethyl-quinolizidine) | 100 | 166 |
| 5 | CH₃CO | H | H | ~~NEt₂ | 100 | 102 |
| 6 | CF₃ | H | H | ~~NEt₂ | 100 | 84 |
| 7 | CF₃ | H | H | ~~~NEt₂ | 95 | 28 |
| 8 | NO₂ | H | H | ~~NEt₂ | 91 | 127 |
| 9 | H | H | H | ~~N⁺(Me)₃ | 100 | 236 |
| 10 | H | H | H | ~~N(i-Pr)₂ | 55 | 42 |
| 11 | Me | Me | H | ~~NMe₂ | 100 | 92 |
| 12 | Cl | Cl | H | ~~NMe₂ | 97 | 18 |
| 13 | H | H | Me | ~~NMe₂ | 90 | 118 |
| 14 | H | H | H | ~~N(pyrrolidine) | 90 | 80 |
| 15 | H | H | H | ~~N(piperidine) | 92 | 75 |
| 16 | H | H | H | ~~N(azepane) | 73 | 67 |
| 17 | H | H | H | (S)-2-ethyl-1-methylpyrrolidine | 53 | 24 |
| 18 | H | H | H | (R)-2-ethyl-1-methylpyrrolidine | 54 | 105 |

TABLE 1-continued
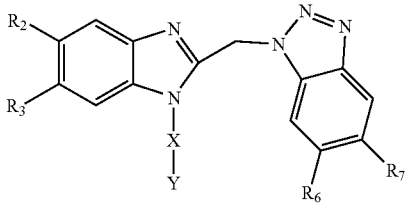
| Example No. | R2 | R3 | R6 and R7 | X—Y | % Cell protection at 4 μg/mL | CC50 (μM) |
|---|---|---|---|---|---|---|
| 19 | H | H | H |  | 95 | 12 |
| 20 | H | H | H | 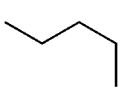 | 87 | 40 |
| 21 | H | H | H | 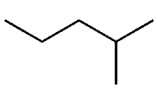 | 98 | 69 |
| 22 | H | H | H | 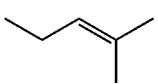 | 75 | 15 |
| 23 | H | H | H | 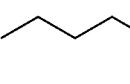 | 98 | 59 |
| 24 | H | H | H | 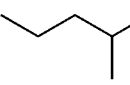 | 100 | 165 |
| 25 | H | H | H | 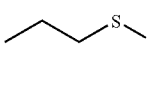 | 100 | 56 |
| 26 | H | H | H | 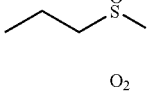 | 100 | 200 |
| 27 | H | H | H | 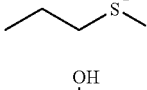 | 44 | 117 |
| 28 | H | H | H | 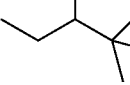 | 61 | 29 |
| 29 | H | H | H | 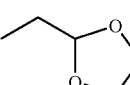 | 98 | 185 |
| 30 | H | H | H | 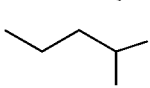 | 90 | 108 |
| 31 | H | H | H | 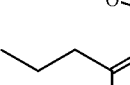 | 48 | 21 |
| 32 | H | H | H | 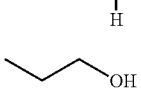 | 60 | 71 |
| 33 | H | H | H | 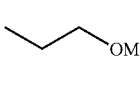 | 82 | 75 |

TABLE 1-continued

| Example No. | R₂ | R₃ | R₆ and R₇ | X—Y | % Cell protection at 4 μg/mL | CC₅₀ (μM) |
|---|---|---|---|---|---|---|
| 34 | H | H | H | propyl-NH₂ | 81 | 86 |
| 35 | H | H | H | -CH₂CH₂-C(=O)-NH-CH₃ | 58 | 230 |
| 36 | H | H | H | -CH₂CH₂CH₂-NH-CH₃ | 100 | 74 |
| 37 | H | H | H | -CH₂CH₂CH₂-C(=O)-CH₃ | 100 | 59 |
| 38 | H | H | H | -CH₂CH₂CH₂-CH(OH)-CH₃ | 100 | >309 |
| 39 | H | H | H | -CH₂CH₂CH₂-C(=N-OH)-CH₃ | 100 | >33 |
| 40 | H | H | H | -CH₂CH₂CH₂-CH(NHCH₃) | 96 | 8.5 |
| 41 | H | H | H | -CH₂CH₂CH₂-C(=O)-NH₂ | 75 | 4.3 |
| 42 | H | H | H | -CH₂CH₂CH₂-C(=O)-O-C(CH₃)₃ | 100 | 168 |
| 43 | H | H | H | -CH₂CH₂CH₂-C(=O)-OH | 82 | >309 |
| 44 | H | H | H | -CH₂CH₂CH₂-C(=N-OH)-NH₂ | 91 | 16 |
| 45 | H | H | H | -CH₂CH₂CH₂-C(=NH)-NH₂ | 74 | 6.3 |
| 46 | H | H | H | -CH₂-phenyl | 53 | 97 |

TABLE 1-continued

Structure: benzimidazole-CH2-benzotriazole with R2, R3 on benzimidazole, R6, R7 on benzotriazole, and X—Y substituent on benzimidazole N.

| Example No. | R2 | R3 | R6 and R7 | X—Y | % Cell protection at 4 µg/mL | CC50 (µM) |
|---|---|---|---|---|---|---|
| 47 | H | H | H | (ethyl-pyridin-3-yl) | 40 | 250 |
| 48 | H | H | H | (n-propyl-phenyl) | 95 | 2.6 |
| 49 | H | H | H | (2-oxo-2-phenylethyl, propiophenone) | 76 | 18 |
| 50 | H | H | H | (1-hydroxy-1-phenylpropyl) | 94 | 36 |

TABLE 2

Structure: benzimidazole-CH2-(2H-benzotriazole) with R2 on benzimidazole, X—Y on benzimidazole N.

| Example No. | R2 | X—Y | % Cell protection at 4 µg/mL | CC50 (µM) |
|---|---|---|---|---|
| 51 | H | (CH2)3NMe2 | 100 | 212 |
| 52 | H | (CH2)4NMe2 | 89 | 182 |
| 53 | H | (CH2)3NEt2 | 78 | 83 |
| 54 | Cl | (CH2)3NEt2 | 100 | 82 |
| 55 | CH3CO | (CH2)4NEt2 | 56 | 185 |
| 56 | CF3 | (CH2)3NEt2 | 83 | 99 |
| 57 | H | (CH2)3N(i-Pr)2 | 100 | 42 |
| 58 | H | (CH2)3-pyrrolidin-1-yl | 92 | 140 |
| 59 | H | (CH2)3-piperidin-1-yl | 87 | 65 |

TABLE 2-continued

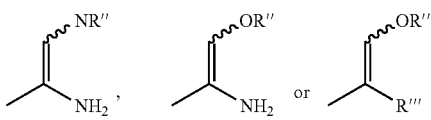

| Example No. | R₂ | X—Y | % Cell protection at 4 µg/mL | $CC_{50}$ (µM) |
|---|---|---|---|---|
| 60 | H | | 77 | 23 |
| 61 | H | | 78 | 27 |

What is claimed is:

1. A method for treating mammals infected with RSV comprising the administration of a therapeutically effective amount of a compound having the Formula II or Formula III, or a pharmaceutically acceptable salts thereof,

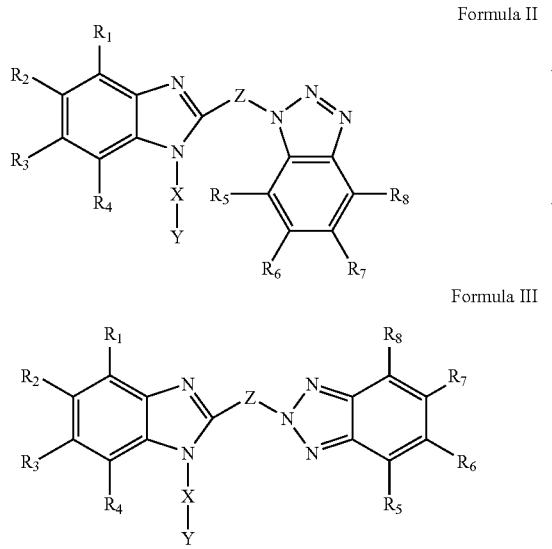

Formula II

Formula III wherein:

$R_1$, $R_2$, $R_3$, $R_4$, $R_5$, $R_6$, $R_7$ and $R_8$ are independently H, alkyl, alkyl substituted with 1 to 6 halogen atoms, $NO_2$, CN, halogen, COR', COOR', and CONHR', R' is H or alkyl, and said alkyl contains 1 to 6 carbon atoms;

X is straight, branched or cyclic alkylene group optionally containing one unsaturation double or triple bond, wherein said groups has 2 to 12 carbon atoms;

Y is selected from:

(a) $R_9$, —$NR_9R_{10}$, —$^+NR_9R_{10}R_{11}$, —$NHCOR_9$, =N—O—$R_9$; —$CONHR_9$, —$COOR_9$, —CO—$R_9$, —$OR_9$, wherein $R_9$, $R_{10}$ and $R_{11}$ are independently H, straight, branched or cyclic alkyl containing 1 to 7 carbon atoms; or $R_9$ taken together with $R_{10}$ forms a cyclic alkyl group having 3 to 7 carbon atoms;

(b) —$N_3$, —CN, halogen, —$NO_2$, —NR"$SO_2$R'", —SR", —SOR", —$SO_2$R", —$SO_2$NR",

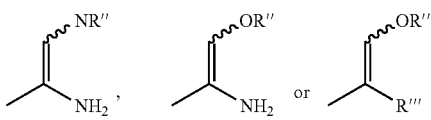

wherein said R" and R'" are independently hydrogen, $C_1$–$C_6$ alkyl, phenyl, or phenyl substituted with from 1 to 6 halogen atoms or $C_1$–$C_6$ alkyl groups;

(c) phenyl or heterocycle, selected from dioxolane, pyridine, pyrrole, thiophene, pyrrolidine or piperidine, and wherein said phenyl is optionally substituted with from 1 to 6 halogen atoms or $C_1$–$C_6$ alkyl groups;

or X and Y taken together is selected from —$CH_2Ph$, —$CH_2COPh$, —$CH_2CHOHPh$,

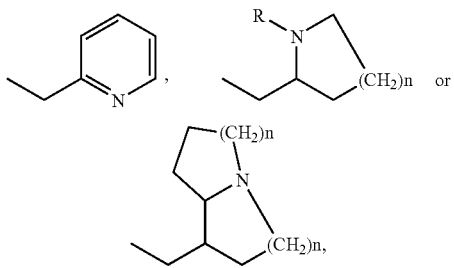

wherein n is 1 or 2, R is $C_1$–$C_4$ alkyl and Ph is phenyl; and

Z is —$(CR_{12}R_{13})_n$—, wherein n is 1–4, and $R_{12}$ and $R_{13}$ are independently H, straight, branched or cyclic $C_1$–$C_6$ alkyl.

* * * * *